US008314466B2

(12) United States Patent
Nakatani et al.

(10) Patent No.: US 8,314,466 B2
(45) Date of Patent: Nov. 20, 2012

(54) SILICON STRUCTURE, METHOD FOR MANUFACTURING THE SAME, AND SENSOR CHIP

(75) Inventors: Masaya Nakatani, Hyogo (JP); Hiroshi Ushio, Osaka (JP); Soichiro Hiraoka, Hyogo (JP); Akiyoshi Oshima, Osaka (JP); Makoto Takahashi, Osaka (JP)

(73) Assignee: Panasonic Corporation, Osaka (JP)

( * ) Notice: Subject to any disclaimer, the term of this patent is extended or adjusted under 35 U.S.C. 154(b) by 294 days.

(21) Appl. No.: 12/676,826

(22) PCT Filed: Sep. 4, 2008

(86) PCT No.: PCT/JP2008/002430
§ 371 (c)(1),
(2), (4) Date: Mar. 5, 2010

(87) PCT Pub. No.: WO2009/034697
PCT Pub. Date: Mar. 19, 2009

(65) Prior Publication Data
US 2010/0219488 A1 Sep. 2, 2010

(30) Foreign Application Priority Data

Sep. 11, 2007 (JP) ................................. 2007-234935
Sep. 21, 2007 (JP) ................................. 2007-244829
Oct. 15, 2007 (JP) ................................. 2007-267596

(51) Int. Cl.
*H01L 27/14* (2006.01)
*H01L 29/82* (2006.01)
*H01L 29/84* (2006.01)
*H01L 21/00* (2006.01)
*C23C 16/00* (2006.01)

(52) U.S. Cl. .................. 257/414; 257/E29.166; 438/85; 427/248.1
(58) Field of Classification Search .................. 257/414, 257/E29.166; 438/85; 427/248.1
See application file for complete search history.

(56) References Cited

U.S. PATENT DOCUMENTS
5,183,744 A 2/1993 Kawamura et al.
(Continued)

FOREIGN PATENT DOCUMENTS
EP 0 652 308 B1 3/2002
(Continued)

OTHER PUBLICATIONS

T. Sordel et al., "Silicon-Based Multi-Patch Device: Application for Ionic Currents Sensoring on Single Cells,"8th International Conference on Miniturized Systems for Chemistry and Life Sciences, 2004, pp. 520-522.

(Continued)

*Primary Examiner* — David S Blum
(74) *Attorney, Agent, or Firm* — McDermott Will & Emery LLP

(57) ABSTRACT

A silicon structure of the present invention is provided with a silicon substrate (1) to become a base, and a plurality of fibrous projections (2) made of silicon dioxide and directly joined to a silicon-made surface (1*a*) of the silicon substrate (1). By arbitrarily constructing an area where these fibrous projections (2) are formed in a predetermined area, it is possible to render the area to have at least either hydrophilicity or water retentivity, so as to provide a silicon structure useful for a variety of devices.

12 Claims, 18 Drawing Sheets

U.S. PATENT DOCUMENTS

| | | |
|---|---|---|
| 6,682,649 B1 | 1/2004 | Petersen et al. |
| 6,984,297 B2 | 1/2006 | Nisch et al. |
| 7,006,929 B2 | 2/2006 | Oka et al. |
| 7,501,278 B2 | 3/2009 | Nakatani et al. |
| 2001/0046706 A1 | 11/2001 | Rubinsky et al. |
| 2002/0074227 A1 | 6/2002 | Nisch et al. |
| 2003/0107386 A1 | 6/2003 | Dodgson et al. |
| 2003/0113833 A1 | 6/2003 | Oka et al. |
| 2004/0033483 A1 | 2/2004 | Oka et al. |
| 2004/0175844 A1 | 9/2004 | Yang et al. |
| 2004/0262636 A1 | 12/2004 | Yang et al. |
| 2005/0038498 A1 | 2/2005 | Dubrow et al. |
| 2005/0221072 A1 | 10/2005 | Dubrow et al. |
| 2005/0221469 A1 | 10/2005 | Nakatani et al. |
| 2006/0043555 A1* | 3/2006 | Liu ............................... 257/680 |
| 2006/0159916 A1 | 7/2006 | Dubrow et al. |
| 2006/0163063 A1 | 7/2006 | Picollet-Dahan et al. |
| 2006/0204738 A1 | 9/2006 | Dubrow et al. |
| 2007/0282247 A1 | 12/2007 | Desai et al. |

FOREIGN PATENT DOCUMENTS

| | | |
|---|---|---|
| FR | 2 844 052 | 3/2004 |
| JP | 2-131596 | 5/1990 |
| JP | 06-244257 | 9/1994 |
| JP | 2000-243700 | 9/2000 |
| JP | 2003-511668 | 3/2003 |
| JP | 2003-511699 | 3/2003 |
| JP | 2004-012215 | 1/2004 |
| JP | 2004-069309 | 3/2004 |
| JP | 2004-271330 | 9/2004 |
| JP | 2004-271331 | 9/2004 |
| WO | WO 02/055653 A1 | 7/2002 |
| WO | WO 02/099408 A1 | 12/2002 |
| WO | WO 03/016555 A1 | 2/2003 |
| WO | WO 2004/038410 | 5/2004 |
| WO | WO 2004/099068 A2 | 11/2004 |
| WO | WO 2005/004197 A2 | 1/2005 |
| WO | WO 2007/046432 A1 | 4/2007 |

OTHER PUBLICATIONS

Japanese Office Action issued in Japanese Patent Application No. 2010-186807, dated Mar. 29, 2011.

International Search Report issued in International Patent Application No. 05765636.5 dated Jan. 30, 2012.

* cited by examiner

SILICON STRUCTURE, METHOD FOR MANUFACTURING THE SAME, AND SENSOR CHIP

RELATED APPLICATIONS

This application is the U.S. National Phase under 35 U.S.C. §371 of International Application No. PCT/JP2008/002430, filed on Sep. 4, 2008, which in turn claims the benefit of Japanese Application Nos. 2007-234935, filed on Sep. 11, 2007, 2007-244829, filed on Sep. 21, 2007 and 2007-267596, filed on Oct. 15, 2007, the disclosures of which Applications are incorporated by reference herein.

TECHNICAL FIELD

The present invention relates to a silicon structure required to have at least either hydrophilicity or water retentivity, a method for manufacturing the same, and a sensor chip, having a silicon structure and being used for a cellular electrophysiological sensor, of a variety of sensors, actuators, electronic devices and the like, which use silicon.

BACKGROUND ART

Recently, an MEMS (Micro Electro Mechanical Systems) device using a silicon material for measuring a biochemical reaction has become a focus of attention.

For example disclosed has been a technique of providing plural through holes in a cell holding substrate, making a sample cell closely adhere to an opening of the through hole, and measuring a potential-dependent ion-channel activity of the sample cell with a measurement electrode arranged below the through hole.

Further disclosed has been a technique of forming a 2.5-µm through hole (hole) inside a cell holding substrate (membrane) made of silicon oxide, and making this through hole hold HEK293 cell as a kind of human cultured cell lines, to ensure high adhesiveness and measure an extracellular potential with high accuracy (e.g., refer to Non-Patent Document 1).

For such a structure used for such a cell holding substrate, a silicon material broadly in use in the field of the semiconductor technology is preferably used from the viewpoints of processability and productivity.

The surface of the silicon material used for a device made up of such a structure preferably has hydrophilicity or water retentivity, and in some cases, it is required to have both the hydrophilicity and the water retentivity. For the purpose of making the surface of the silicon material hydrophilic, a technique of forming a thin film of an inorganic oxide on the surface of the silicon material by sputtering has been disclosed (e.g., refer to Patent Document 1).

However, with the conventional configuration, imparting the hydrophilicity has been possible, but imparting the water retentivity has not been possible. Further, although it is required to form an area having the hydrophilicity or the water retentivity in a restricted specific area, it has been particularly difficult to form the area having the water retentivity in a restricted area.

Incidentally, living matters including humans organize a variety of cells to conduct activities. As a mechanism for transmitting stimulus information, received by a cell (e.g. visual cell) in some tissue from the outside, to another tissue cell (e.g. nerve), ion channels are present as a kind of functional proteins. These ion channels reside in cell membranes of every kind, and undertake an important role of allowing passage of ions (e.g. $Na^+$, $K^+$, $Ca^{2+}$, etc.) between the inside and outside of the cell, to generate a current to be transmitted between cells or a potential difference.

In recent years, it has become possible, by finding out details of actions of these ion channels, to measure an effect of a new medicine at a cellular level or to measure the presence or absence of a side effect. While a variety of methods for measuring ion channels are present, a patch clamp technique has been the most used method since being capable of accurately measuring actions of ion channels in a single cell. Among the back clamp techniques, a planar patch technique capable of holding cells on a plane substrate has been a great focus of attention as being effective in increasing a throughput of measurement.

In this planer patch technique, a cellular electrophysiological sensor is used as a sensor portion for holding and electrically measuring a cell. As a sensor chip for this cellular electrophysiological sensor, the foregoing structure using the silicon material (hereinafter referred to as a "silicon structure") can be employed.

An example of conventional cellular electrophysiological sensors is described in further details. FIG. 37 shows a sectional view of a conventional cellular electrophysiological sensor. As shown in FIG. 37, sensor chip 201 for the cellular electrophysiological sensor is provided with thin plate 203 having conduction hole 202, and frame body 204 arranged on this thin plate 203, and has cavity 205 inside frame body 204. Further, these thin plate 203 and frame body 204 have been processed using silicon material with high accuracy.

The cellular electrophysiological sensor using this sensor chip 201 is provided with: chip holding plate 206 with sensor chip 201 inserted therein; electrolytic baths 207, 208 arranged above and below sensor chip 201; and electrodes 209, 210 respectively arranged inside these electrolytic baths 207, 208.

In this cellular electrophysiological sensor, each of electrolytic baths 207, 208 is filled with an electrolyte, and cells 211 are then injected into upper electrolytic bath 207. Subsequently, by absorbing the electrolyte or the like downward from lower electrolytic bath 208 or performing some other operation, cell 211 can be captured at an opening of conduction hole 202. A potential difference between electrolytic baths 207, 208, a current, a resistance or the like can then be measured, so as to measure physicochemical changes during activities of cells 211, namely actions of ion-channels.

Here, it is required in the measurement that each of top and under surfaces of sensor chip 201 be filled with the electrolyte. However, since the surface is made of a hydrophobic silicon base, it is difficult to fill the inside of cavity 205 with the electrolyte. Therefore, as a method for rendering sensor chip 201 hydrophilic, there exists a method of thermally treating sensor chip 201 to form hydrophilic thermally oxidized film 212 on the surface of the silicon base.

It is to be noted that a similar example to above sensor chip 201 is disclosed in Patent Document 2 mentioned below.

However, there has been a problem with conventional sensor chip 201 in that measurement accuracy of the cellular electrophysiological sensor may decrease.

The reason for this is that bubble 213 may be generated inside cavity 205 of frame body 204 depending upon a difference in environment where measurement is performed.

Specifically, even when thermally oxidized film 212 is formed on an inner wall of frame body 204, an organic matter or the like adheres to the surface of the film with time, to lower the hydrophilicity. This makes bubble 213 apt to be generated inside cavity 205, and due to the presence of bubble 213, electrical conduction between the above and below conduction hole 202 is inhibited, or infiltration of a medicine is
} inhibited. As a consequence, there has been a problem in that the measurement accuracy of the cellular electrophysiological sensor decreases.

Moreover, another example of the conventional cellular electrophysiological sensors is described in further details. FIG. 38 shows a sectional view of a conventional cellular electrophysiological sensor. As shown in FIG. 38, sensor chip 301 for the conventional cellular electrophysiological sensor is provided with thin plate 303 having conduction hole 302, and frame body 304 arranged on this thin plate 303, and these thin plate 303 and frame body 304 have been processed using the silicon material with high accuracy.

Cellular electrophysiological sensor 305 using this sensor chip 301 is provided with: chip holding plate 306 with sensor chip 301 inserted therein; electrolytic baths 307a, 307b arranged above and below sensor chip 301; and electrodes 308a, 308b respectively arranged inside these electrolytic baths 307a, 307b.

In this cellular electrophysiological sensor 305, each of electrolytic baths 307a, 307b is filled with an electrolyte, and cells 309 are then injected into upper electrolytic bath 307a. Subsequently, by absorbing the electrolyte or the like downward from lower electrolytic bath 307b or performing some other operation, cell 309 can be captured at an opening of conduction hole 302. A potential difference between electrolytic baths 307a, 307b, a current, a resistance or the like can then be measured, so as to measure physicochemical changes of cells 309 during activities of cells 309, namely actions of ion-channels.

Here, it is required that each of top and under surfaces of sensor chip 301 be filled with the electrolyte. However, since the surface is made of a silicon base that is apt to be hydrophobic, a bubble may be generated on the under surface of sensor chip 301. As a method for rendering the surface of sensor chip 301 hydrophilic to prevent generation of this bubble, there exists a method of thermally treating sensor chip 301 to form hydrophilic thermally oxidized film 310 on its surface.

It is to be noted that a similar example to above sensor chip 301 is disclosed in Patent Document 1 mentioned below.

However, there has been a problem with conventional sensor chip 301 in that measurement accuracy of cellular electrophysiological sensor 305 may decrease.

The reason for this is that a bubble may be generated on under surface 303a of thin plate 303 depending upon a difference in environment where measurement is performed.

Specifically, even when thermally oxidized film 310 is formed on under surface 303a of thin plate 303, an organic matter or the like adheres to the surface of the film with time, whereby the hydrophilicity decreases and bubble 312 is then generated. When, as a consequence, this bubble 312 adheres to the vicinity of lead-out port 311 of conduction hole 302, electrical conduction between above and below conduction hole 302 is inhibited.

Consequently, there has been a problem in that the measurement accuracy of cellular electrophysiological sensor 305 decreases.

[Non-Patent Document 1] "Micro Total Analysis Systems 2004", T. Sordel et al., pp-521-522 (2004)
[Patent Document 1] Unexamined Japanese Patent Publication No. 2000-243700
[Patent Document 2] Unexamined Japanese Patent Publication No. 2004-69309

DISCLOSURE OF THE INVENTION

The present invention provides a silicon structure, which is provided with fibrous projections made of silicon dioxide on its surface made of silicon, to selectively form an area having at least either hydrophilicity or water retentivity, and a method for manufacturing the same.

Further, the present invention provides a sensor chip, including a silicon structure and capable of improving measurement accuracy of a cellular electrophysiological sensor.

Specifically, a silicon structure of the present invention includes a base, and plural fibrous projections made of silicon dioxide on a silicon-made surface of this base, and these plural fibrous projections are configured to be directly joined to the surface.

In this manner, one ends of the fibrous projections made of silicon dioxide are formed by direct joining on the surface of the silicon structure, whereby an area where these fibrous projections are formed is configured to selectively have at least either hydrophilicity or water retentivity.

Further, a method for manufacturing a silicon structure according to the present invention includes: a first step of forming a seed layer made of an organic polymer in an arbitrary area on a silicon-made surface of a base; and a second step of heating the base in an oxygen atmosphere, to form plural fibrous projections made of silicon dioxide in the area where the seed layer is formed.

With such a method performed, the plural fibrous projections can be formed by direct joining in a predetermined area on the surface of the base, so that silicon dioxide that forms the plural fibrous projections has a large surface area. It is thereby possible to manufacture a silicon structure capable of exerting at least either hydrophilicity or water retentivity which is high as a whole.

Further, a sensor chip in the present invention is provided with: a thin plate having a conduction hole; and a frame body arranged on this thin plate, a cell capturing face of the thin plate is formed of a silicon dioxide layer, while an inner wall of the frame body is formed of a silicon layer, and plural fibrous projections made of silicon dioxide are directly joined to the inner wall of the frame body.

With such a configuration formed, the fibrous projections having the hydrophilicity and a very large surface area are provided on the inner wall of the frame body so that bubbles which are generated inside a cavity of the frame body can be reduced. Therefore, using the sensor chip of the present invention for a cellular electrophysiological sensor or the like can significantly improve the measurement accuracy.

Further, a sensor chip of the present invention is provided with: a thin plate having a conduction hole; and a frame body arranged on this thin plate, the thin plate is made up of a laminated body of a silicon layer and a silicon dioxide layer formed on this silicon layer, and plural fibrous projections made of silicon dioxide are directly joined to the under surface of the silicon layer.

With such a configuration formed, fibrous projections having the hydrophilicity and a very large surface area are provided on the under surface of a thin plate so that bubbles which are generated on the under surface can be reduced. Therefore, using the sensor chip of the present invention for a cellular electrophysiological sensor or the like can significantly improve the measurement accuracy.

Figure 1:
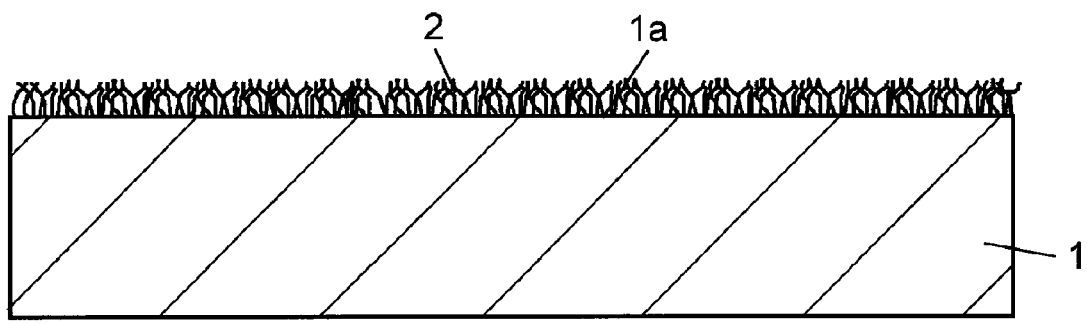
FIG. 1 is a sectional view of a silicon structure in a first embodiment of the present invention.

REFERENCE MARKS IN THE DRAWINGS 1, 6 Silicon substrate (Base)
1a, 6a Surface
1b, 6b Predetermined area
2, 7, 22, 121 Fibrous projections
3, 8 Resist film
4, 28, 128 Seed layer
5 Silicon dioxide thin film
14, 113 Sensor chip
15, 114 Thin plate
16, 115 Frame body
16a Inner wall
17, 116 Cavity
18 Second Silicon layer (Silicon layer)
19, 113a Cell capturing face
20, 118 Silicon dioxide layer
21, 120 Conduction hole
23, 122 Chip holding plate (Holding plate)
24a, 24b, 123a, 123b Electrolytic bath
25a, 25b, 124a, 124b Electrode
26, 125 Cell
27 First silicon layer (Silicon layer)
29, 31, 130, 133 Protective layer
30 Thermally oxidized film
117, 126 Silicon layer
117a Under surface
119 Concave section
120a Opening
120b Lead-out port
127 Mask 129 Area where fibrous projections are desired to be left
131 Area where fibrous projections are desired to be removed
132 Area where fibrous projections are not to be formed

PREFERRED EMBODIMENTS FOR CARRYING OUT OF THE INVENTION

An embodiment of the present invention is described below with reference to the drawings. It is to be noted that, since like elements are denoted by like reference numerals, there are cases where their description is omitted.

First Embodiment

Hereinafter, a silicon structure and a method for manufacturing the same according to a first embodiment of the present invention are described with reference to the drawings.

Figure 2:
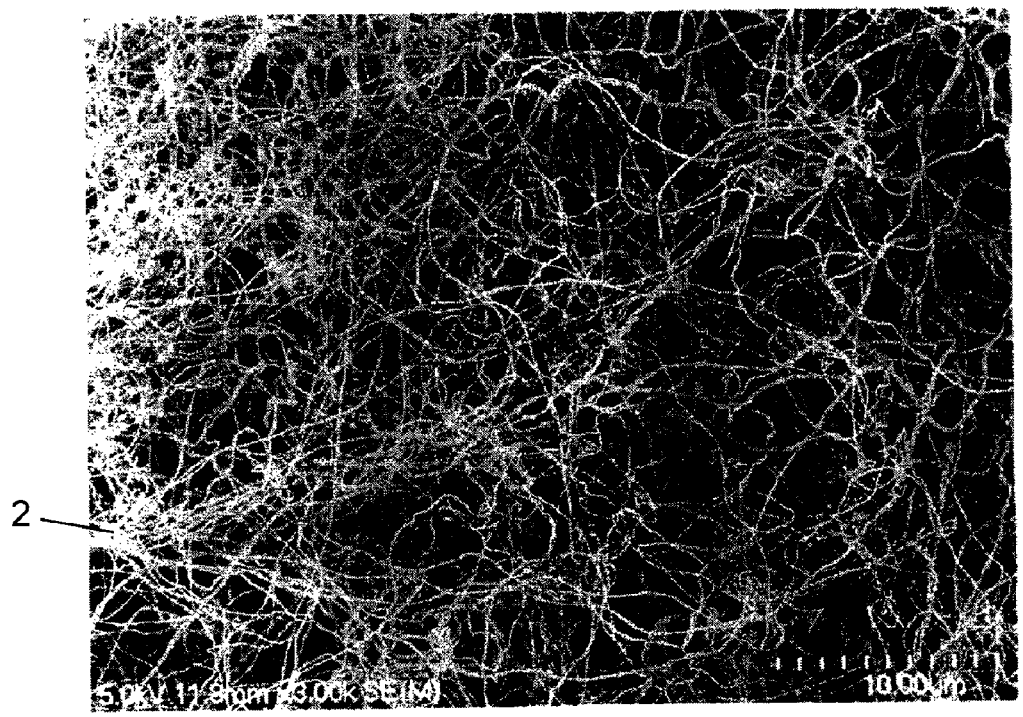
FIG. 2 shows an SEM (Scanning Electron Microscope) photograph of a surface of the silicon structure in the first embodiment of the present invention.

FIG. 1 is a sectional view of a silicon structure in the first embodiment of the present invention, and FIG. 2 is an SEM photograph showing the surface state of the silicon structure of FIG. 1. Those that are white and densely formed as entwined with one another are fibrous projections 2.

As shown in FIGS. 1 and 2, the silicon structure of the present invention is provided with: base 1; and plural fibrous projections 2 which are made of silicon dioxide and directly joined to silicon-made surface 1a of this base 1. Here, base 1 may be a substrate containing silicon, and in the present embodiment, for example, silicon substrate 1 is used. It is to be noted that one ends of fibrous projections 2 are directly joined to surface 1a of silicon substrate 1. In this manner, fibrous projections 2 made of silicon dioxide are formed in moquette form or mesh form as plural fibrous projections 2. Therefore, in this area, a surface area of silicon dioxide is extremely large. In such an area having a large surface area, a liquid material to which large surface tension of silicon dioxide is applied, such as water, is strongly pulled to the surface of silicon dioxide, and the water is then held on a periphery of fibrous projections 2.

Next described is a reason for fibrous projections 2 in the first embodiment of the present invention having large hydrophilicity and water retentivity. Silicon dioxide is essentially a highly hydrophilic material. However, when silicon dioxide is formed into a thin film and contamination from the outside such as air adheres to its surface, surface tension of the thin film made of silicon dioxide, which pulls water, decreases. Therefore, when the thin film has a small surface area, this results in relatively a considerable loss of the hydrophilicity.

As opposed to this, fibrous projections 2 in the silicon structure shown in FIGS. 1 and 2 of the first embodiment of the present invention have an extremely large surface area. For this reason, even when the surface tension per predetermined area decreases due to adhesion of contamination, the tension that pulls water is hardly lost since the whole surface area is large. Consequently, it is possible to realize a silicon structure capable of holding the hydrophilicity and the water retentivity for a long period of time.

Further, fibrous projections 2 are formed by direct joining on the surface of silicon substrate 1, whereby it is possible to simply form fibrous projections 2 without use of an adhesive or the like, and also to enhance thermal resistance. In the meantime, due to non-use of the adhesive or the like which may contain a substance to become impurities for the silicon structure, it is possible to realize a silicon structure with impurities or the like not mixed therein.

Moreover, foregoing fibrous projections 2 are preferably previously formed in moquette form or mesh form on the surface of silicon substrate 1. It is thereby possible to make a surface area per unit area very large, so as to enhance the hydrophilicity and the water retentivity.

It is preferable that an optimal length of fibrous projections 2 be in the range of not smaller than 1.0 μm and not larger than 200 μm, and a spacing at which fibrous projections 2 are joined be in the range of not smaller than 1 μm and not larger than 10 μm. When the length is smaller than 1.0 μm or the spacing is smaller than 1 μm, it is only that a condition for producing fibrous projections 2 becomes difficult, and the water retentivity remains almost unchanged. Moreover, when the length exceeds 200 μm, fibrous projections 2 are apt to be broken. When the spacing exceeds 10 μm, the water retentivity slightly decreases. Therefore, as described above, increasing the length and reducing the spacing can enhance both the hydrophilicity and the water retentivity.

Then, a thickness of these fibrous projections 2 is preferably not smaller than 0.01 μm and not larger than 1 μm. This thickness can be appropriately selected from the viewpoint of the productivity and strength. The numerical range can be decided based upon a degree of required performance of the device, such as holding of high hydrophilicity or water retentivity, or both high hydrophilicity and water retentivity, desired to be imparted to the area where fibrous projections 2 are formed.

Further, these fibrous projections 2 are densely formed as entwined with one another in a moderately curled state. Moreover, the spacing between branch sections of fibrous projections 2 is in the range of not smaller than 1.0 μm and not larger than 10 μm. When the spacing exceeds 10 μm, fibrous projections 2 are less apt to be entwined with one another.

The numerical ranges of the density and the spacing are also decided based upon the degree of the hydrophilicity and the water retentivity desired to be imparted, in a similar manner to the case of the thickness mentioned above. It is to be noted that, when fibrous projections 2 are formed by foregoing thermal oxidation, as described later, fibrous projections 2 become amorphous, and thus apt to be curled. The method for producing fibrous projections 2 by thermal oxidation at this time can be controlled, for example by means of a temperature in thermal oxidation, a gas concentration, or the like.

Further, fibrous projections 2 can also be formed so as to be branched off in random directions. In this manner, the hydrophilicity and the water retentivity can further be enhanced. Fibrous projections 2 made of amorphous, having been subjected to thermal oxidation by plasma CVD (Chemical Vapor Deposition) on conditions of a predetermined temperature, gas concentration, and the like, can be formed as branched off in random directions.

Figure 3:
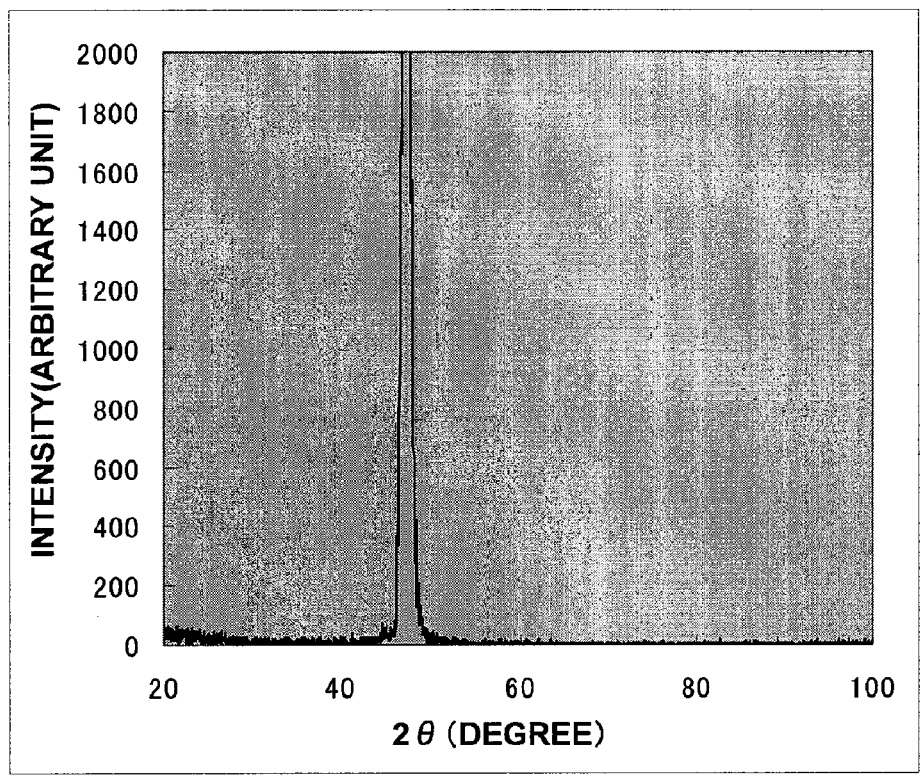
FIG. 3 is a diagram showing a result of an X-ray analysis on fibrous projections of the silicon structure in the first embodiment of the present invention.

FIG. 3 is a diagram showing a result of an X-ray analysis on fibrous projections 2 of the silicon structure in the first embodiment of the present invention. An abscissa axis represents an X-ray diffraction angle 2θ, and an ordinate axis represents an intensity of a diffraction peak in arbitrary units.

In FIG. 3, a peak of fibrous projections 2 is strongly indicated at 47 degrees, which is a peak of Si (110), and no other peaks are found. Further, since being able to be formed by thermal oxidation, fibrous projections 2 is considered to be made of amorphous silicon dioxide and directly joined to surface 1a of silicon substrate 1. It should be noted that fibrous projections 2 made of amorphous silicon dioxide have smaller elasticity than single crystal silicon dioxide as described later, and hence are soft and resistant to breaking.

Next, the method for manufacturing the silicon structure in the first embodiment of the present invention is described with reference to the drawings. FIGS. 4 to 8 are sectional views showing manufacturing steps for explaining the method for manufacturing the silicon structure in the first embodiment of the present invention.

Figure 4:
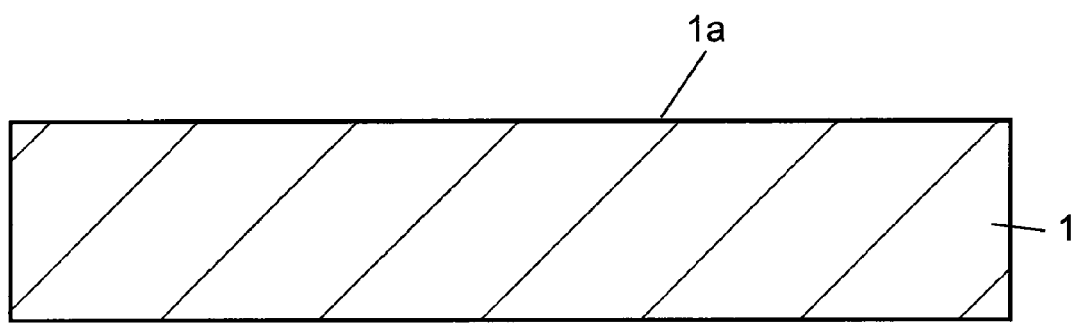
FIG. 4 is a sectional view for explaining a method for manufacturing the silicon structure in the first embodiment of the present invention.

First, as a preparatory step, silicon substrate 1 is prepared as shown in FIG. 4. At this time, the surface of silicon substrate 1 is preferably in a state where silicon atoms are exposed. However, since the surface of silicon substrate 1 with the silicon atoms exposed is apt to be oxidized in the air, silicon dioxide is often formed on surface 1a. Therefore, in use of silicon substrate 1, it is desirable to use one where silicon dioxide formed on surface 1a by native oxidization has a small film thickness.

Figure 5:
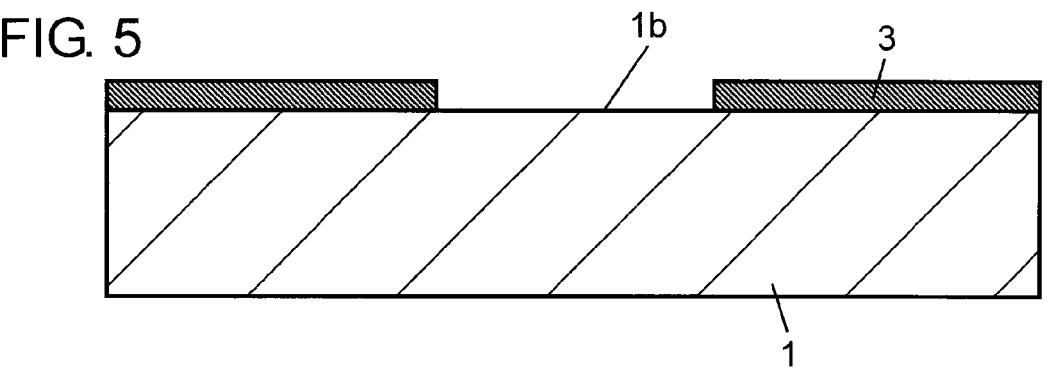
FIG. 5 is a sectional view for explaining the method for manufacturing the silicon structure in the first embodiment of the present invention.

Subsequently, as shown in FIG. 5, resist film 3 is formed such that only predetermined area 1b is exposed. For this resist film 3 used can be a material such as a photoresist typically used for the photolithography technique. This exposed predetermined area 1b is an area where fibrous projections 2 made of silicon dioxide are selectively formed in a later step, and can be selected as an arbitrary area.

Further, areas other than the area where the silicon atoms are exposed are covered with a silicon dioxide thin film in the preparatory step, so that the area where the silicon atoms are exposed can be selectively formed. For example, after a silicon oxide film with a small film thickness is previously formed on surface 1a of silicon substrate 1, the area covered with the silicon dioxide thin film is covered with a resist film or the like, and the silicon dioxide thin film in predetermined area 1b is removed by etching or the like, so that the area where the silicon atoms are exposed can be formed.

Figure 6:
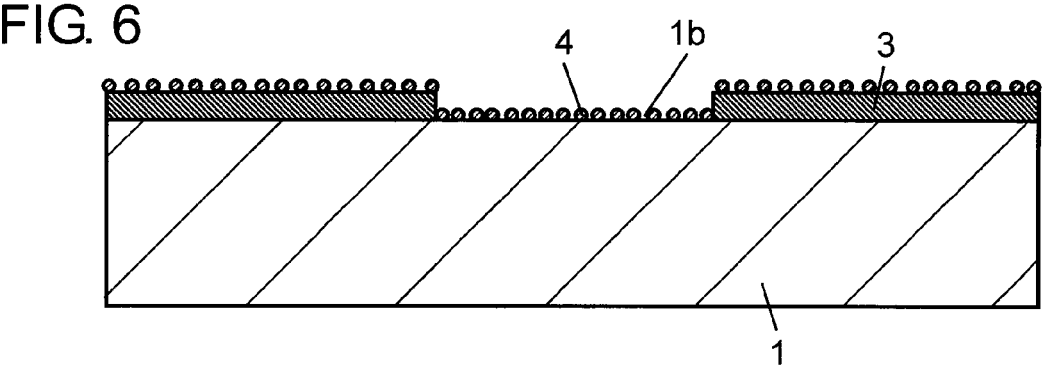
FIG. 6 is a sectional view for explaining the method for manufacturing the silicon structure in the first embodiment of the present invention.

Thereafter, as a first step, as shown in FIG. 6, seed layer 4 containing C, F and H elements is formed in predetermined area 1b on silicon substrate 1. This seed layer 4 is a layer made of an organic polymer containing C (carbon), F (fluorine) and H (hydrogen) elements. It is to be noted that H elements are not essential, and seed layer 4 containing C and F elements may be used. This seed layer 4 can be formed by dissolving at least any gas among fluorocarbon-based gases, such as $CF_4$, $CHF_3$, $C_2F_6$, $C_3F_8$ and $C_4F_8$, in plasma by plasma CVD method.

The foregoing fluorocarbon-based gas is dissolved in plasma into a state where bonds are cut off, such as CF, $CF_2$ and $CF_3$, and these are added with H atoms for recombination, to establish polymer molecules in a variety of combinations. However, in order to form fibrous projections made of silicon dioxide in a later step, the order of combination arrays of these molecules contained in seed layer 4 is not particularly important, and the molecules may just be formed in the state of C, H, F being combined.

The reason for this is presumed to be that, since firing is performed in an oxygen atmosphere at a temperature in the range of 1000° C. to 1100° C. in a later step, molecules in any combination arrays are decomposed due to high heat, and a decomposed matter generated at this time acts to promote generation of the fibrous projections.

Therefore, C, H and F elements at this time are not particularly restricted here since a large number of molecules of C, H and F elements are established as molecules in diverse combinations.

Figure 7:
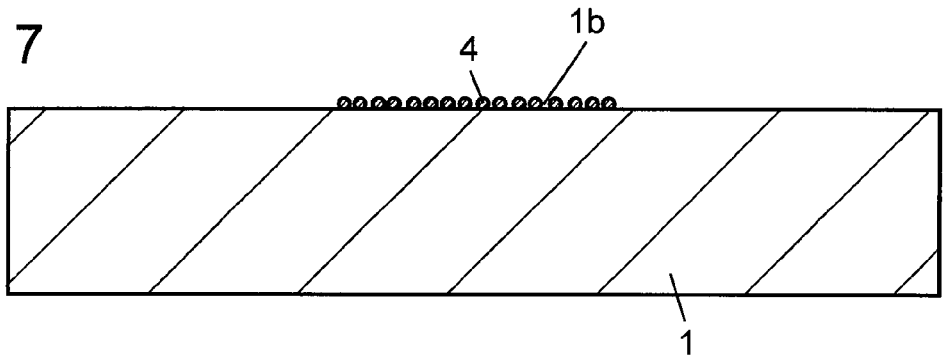
FIG. 7 is a sectional view for explaining the method for manufacturing the silicon structure in the first embodiment of the present invention.

Subsequently, as shown in FIG. 7, resist film 3 is removed. It should be noted that in the process for removing resist film 3 at this time, such a removal method as to make seed layer 4 remain is required. In this regard, the method for forming seed layer 4 by plasma CVD method as in the first embodiment of the present invention is of excellence. In other words, the organic polymer film formed by plasma CVD method has relatively strong medicine resistance, leading to expanded selections of medicines for removing resist film 3.

Further, since this seed layer 4 has the medicine resistance, it is also possible to form seed layer 4 and then process silicon substrate 1 through use of this seed layer 4 as a resist film.

Figure 8:
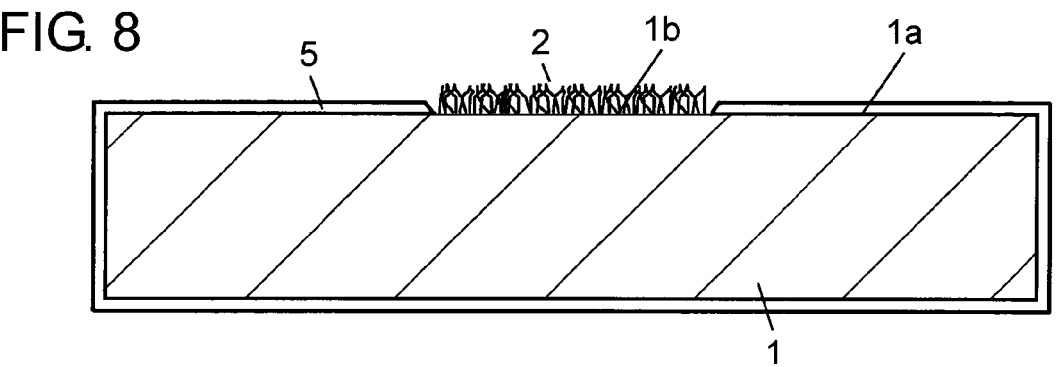
FIG. 8 is a sectional view for explaining the method for manufacturing the silicon structure in the first embodiment of the present invention.

Next, as a second step, as shown in FIG. 8, silicon substrate 1 where seed layer 4 is formed is fired in the oxygen atmosphere at a temperature in the range of 1000° C. to 1100° C. Thereby, plural fibrous projections 2 made of silicon dioxide can be formed only in predetermined area 1b where seed layer 4 is formed. These fibrous projections 2 are bonded to silicon substrate 1 in the state of being directly joined thereto.

As described above, the method for manufacturing the silicon structure according to the present invention includes: the first step of forming seed layer 4 made of the organic polymer in the arbitrary area on silicon-made surface 1a of silicon substrate 1; and the second step of forming plural fibrous projections 2 made of silicon dioxide in the area where seed layer 4 has been formed by heating silicon substrate 1 in the oxygen atmosphere.

With such a method performed, plural fibrous projections 2 can be formed by direct joining in arbitrary predetermined area 1b on surface 1a of silicon substrate 1, so that silicon dioxide that forms plural fibrous projections 2 has a large surface area. It is thereby possible to manufacture a silicon structure capable of exerting at least either hydrophilicity or water retentivity which is high as a whole.

More specifically, in predetermined area 1b where these fibrous projections 2 are formed, each one of fibrous projections 2 made of silicon dioxide has the hydrophilicity, and formed in large number in moquette form or mesh form. Thereby, even when slight surface contamination is generated in the area where fibrous projections 2 made of silicon dioxide are formed, silicon dioxide that forms fibrous projections 2 has a large surface area. Therefore, the silicon structure formed in this manner can exert at least either the hydrophilicity or the water retentivity which is high as a whole.

It is to be noted that in the foregoing manufacturing method, in the second step, silicon dioxide thin film 5 is formed on surface 1a of silicon substrate 1 where resist film 3 have been formed, in addition to fibrous projections 2 made of silicon dioxide, and this silicon dioxide thin film 5 also has the hydrophilicity.

In a case where the configuration of the silicon structure as thus described is not preferred, it is possible to manufacture the silicon structure with the silicon atoms exposed in areas other than predetermined area 1b where fibrous projections 2 are formed by such a manufacturing method as follows. Next, the method for manufacturing the silicon structure is described with reference to FIGS. 9 to 12.

Figure 9:
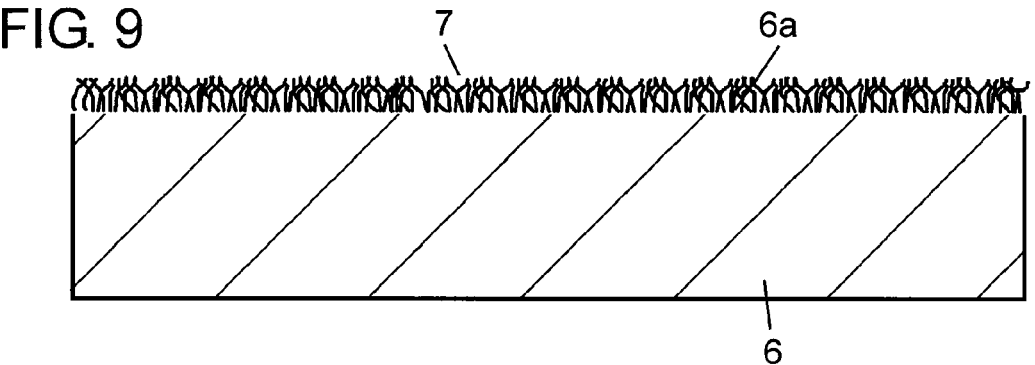
FIG. 9 is a sectional view for explaining another method for manufacturing the silicon structure in the first embodiment of the present invention.

First, as shown in FIG. 9, fibrous projections 7 made of silicon dioxide are formed on at least one surface of silicon substrate 6 where silicon atoms are exposed on surface 6a. This formation method is that, as has already been described, seed layer 4 containing C, H and F is formed on the whole surface of silicon substrate 6, and then fired in the oxygen atmosphere at 1000° C. to 1100° C., to allow the formation.

Figure 10:
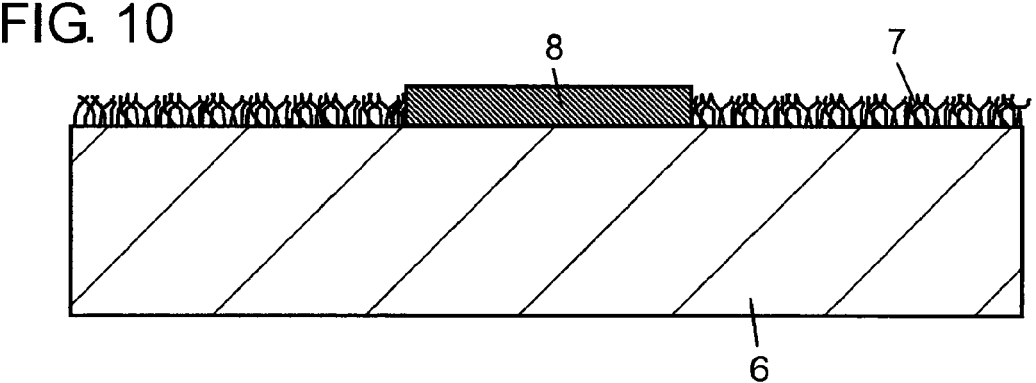
FIG. 10 is a sectional view for explaining another method for manufacturing the silicon structure in the first embodiment of the present invention.

Next, as shown in FIG. 10, resist film 8 is patterned to be formed in an area where fibrous projections 7 made of silicon dioxide are desired to be left.

Figure 11:
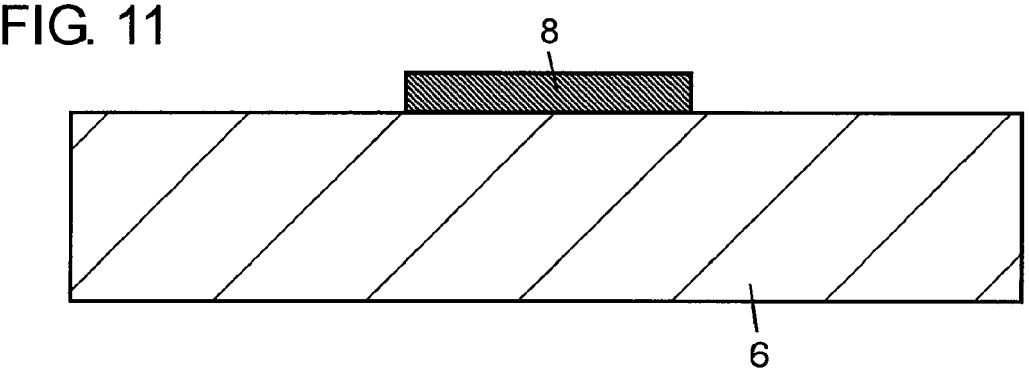
FIG. 11 is a sectional view for explaining another method for manufacturing the silicon structure in the first embodiment of the present invention.

Thereafter, as shown in FIG. 11, fibrous projections 7 made of silicon dioxide are etched using an etching solution of HF, BHF or the like. This is because, as the etching solution for use in this etching, it is preferable to use an etching solution capable of etching silicon dioxide but not capable of etching silicon. Therefore, as such an etching solution, the etching solution of HF, BHF or the like is used.

Figure 12:
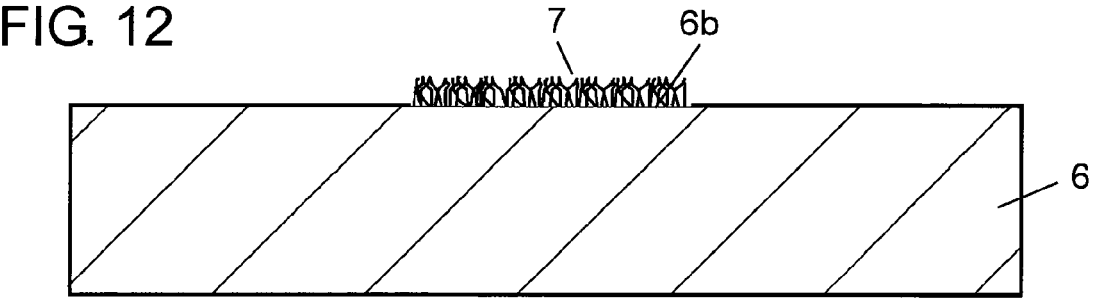
FIG. 12 is a sectional view for explaining another method for manufacturing the silicon structure in the first embodiment of the present invention.

Next, as shown in FIG. 12, resist film 8 is removed using a resist remover or the like. It is thereby possible to form fibrous projections 7 made of silicon dioxide only in predetermined area 6b.

Further, in the foregoing series of manufacturing steps, from the fact that fibrous projections 7 are bonded with silicon substrate 6 with large mechanical strength to prevent a substance that inhibits the hydrophilicity from lying on the interface, it is considered that fibrous projections 7 are covalently bonded to silicon-made surface 6a of silicon substrate 6. Thereby, as described above, fibrous projections 7 have strong resistance to an acidic or alkaline solvent and an organic solvent, and can be easily formed in arbitrary predetermined area 6b on surface 6a of silicon substrate 6.

It should be noted that in this method, the shape of fibrous projections 7 made of silicon dioxide may be destroyed at the time of removal of resist film 8, for example in the case of the length of fibrous projections 7 exceeding 200 µm. Therefore, caution needs to be taken with a viscosity, a film thickness, a drying method, a removal method, and the like regarding the resist agent that forms resist film 8.

By such a manufacturing method, it is possible to manufacture the silicon structure having only fibrous projections 7 in predetermined area 6b of silicon substrate 6 without formation of silicon dioxide thin film 5.

As described above, the silicon structure of the present invention is configured of silicon with a silicon wafer used as a base substrate, whereby it is possible to realize high processability, three-dimensional structure having, for example, a fine groove, hole, concavity, and the like. Further, it is possible to selectively form the silicon structure such that the silicon atoms are partially exposed, thereby to form the structure by selectively directly joining one ends of the fibrous projections made of silicon dioxide only to the portion where these silicon atoms are exposed.

Moreover, in the area where these fibrous projections are formed, it is possible to realize an area having at least either the hydrophilicity or the water retentivity which is extremely high. Since the silicon structure having the hydrophilicity and the water retentivity is realizable in such a selectively restricted area, it is possible to apply the silicon structure to devices required to partially have the hydrophilicity or the water retentivity, even through in complex shape, such as a variety of silicon devices including a biosensor, a chemical reaction chip, and a fluid control device.

Second Embodiment

Figure 13:
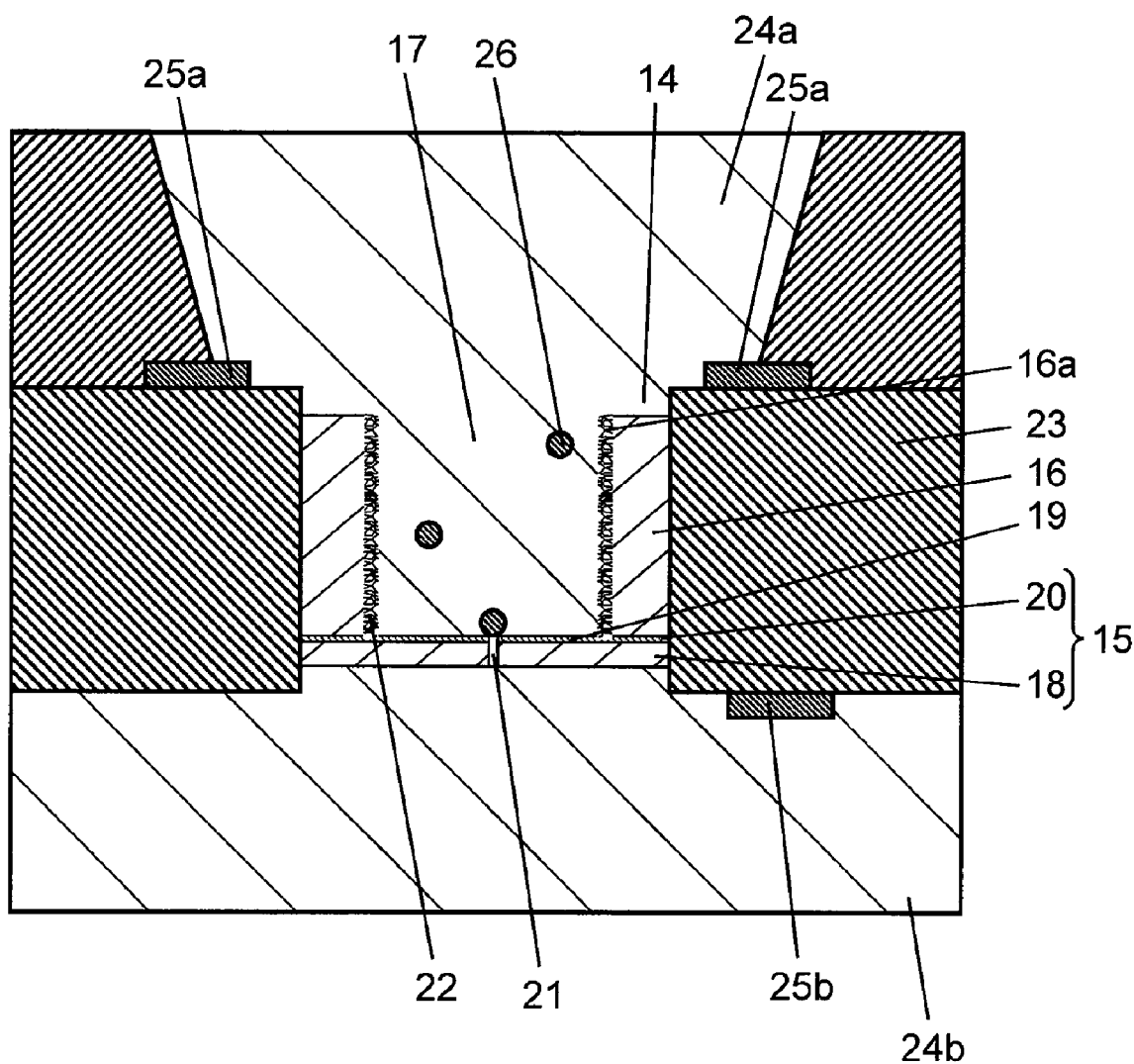
FIG. 13 is a sectional view of a cellular electrophysiological sensor in a second embodiment of the present invention.

FIG. 13 is a sectional view of a cellular electrophysiological sensor in a second embodiment of the present invention. Sensor chip 14 for the cellular electrophysiological sensor shown in FIG. 13 is provided with thin plate 15 and frame body 16 formed and arranged on this thin plate 15. Cell capturing face 19 of this thin plate 15 is formed of silicon dioxide layer 20, while frame body 16 is formed of a silicon layer, and plural fibrous projections 22 made of silicon dioxide are directly joined to inner wall 16a of frame body 16. It is to be noted that a top of frame body 16 is open and an inside of frame body 16 is cavity 17.

This sensor chip 14 is formed of a so-called SOI (Silicon on Insulator) substrate obtained by sandwiching a silicon dioxide layer in the form of a thin film between two silicon layers, and is configured including the silicon structure shown in the first embodiment.

Figure 14:
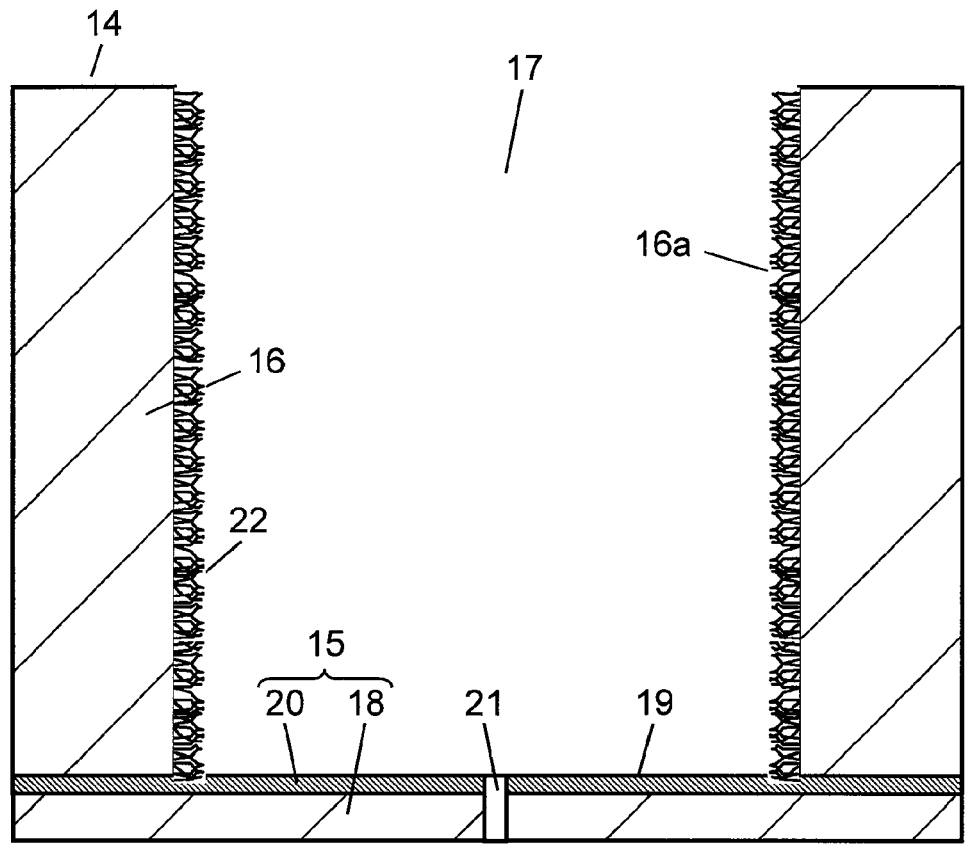
FIG. 14 is a sectional view of a sensor chip in the second embodiment of the present invention.

Specifically, thin plate 15 is made up of a laminated body of: (second) silicon layer 18 to become a bottom surface; and silicon dioxide layer 20 to become cell capturing face 19 of thin plate 15 on this silicon layer 18. Further, frame body 16 is made up of a silicon layer formed on foregoing silicon dioxide layer 20. Moreover, as shown in FIGS. 13 and 14, conduction hole 21 that penetrates thin plate 15 in a vertical direction is formed in this thin plate 15.

Furthermore, in the present embodiment, plural fibrous projections 22 made of silicon dioxide are directly joined to almost the whole area of inner wall 16a of frame body 16. It is to be noted that fibrous projections 22 may be formed not in the whole area of inner wall 16a of frame body 16, but in a partial area as described later.

Moreover, in the present embodiment, for example, silicon layer 18 in thin plate 15 is formed to have a film thickness of about 5.0 µm, silicon dioxide layer 20 is formed to have a thickness of about 2.0 µm, and the silicon layer is formed to have a thickness of about 400 µm.

A diameter and a depth of conduction hole 21 are decided corresponding to a shape of a cell to be captured. Conduction hole 21 shown in FIG. 13 is formed with a diameter being about 3 µM and a depth being about 7.0 µm. This is because, in the case of capturing a cell with a diameter of 10 µm to 20 µm, conduction hole 21 preferably has a diameter of not smaller than 1 µm and not larger than 5 µm, and a depth of not smaller than 1 µm and not larger than 10 µm. Further, thicknesses of silicon layer 18 and silicon dioxide layer 20 in thin plate 15 are also appropriately decided corresponding to the shape of the cell to be captured. However, the thickness of silicon dioxide layer 20 is desirably at least not smaller than 0.1 µm for a reason described later.

Further, in the present embodiment, the overall length of fibrous projections 22 is not smaller than 1.0 µm and not larger than 200 µm, the thickness thereof is not smaller than 0.01 µm and not larger than 10.0 µm, and the spacing between plural fibrous projections 22 is not smaller than 1.0 µm and not larger than 10 µm.

Moreover, these fibrous projections 22 are ones having been grown until being minutely wound or curled in order to have a larger surface area, and fibrous projections 22 each have a wavy shape and are densely formed in a mutually entwined state.

Furthermore, in the present embodiment, sensor chip 14 having the foregoing specific configuration is used for the cellular electrophysiological sensor shown in FIG. 13.

The cellular electrophysiological sensor shown in FIG. 13 is provided with: sensor chip 14; chip holding plate (holding section) 23 into which this sensor chip 14 has been inserted; electrolytic baths 24a, 24b arranged above and below sensor chip 14; and electrodes 25a, 25b respectively arranged in electrolytic baths 24a, 24b.

It is to be noted that, although electrolytic baths 24a, 24b are used as a liquid pooling section for arranging an electrolyte and electrodes 25a, 25b in the present embodiment, electrodes 25a, 25b are not necessarily required to be in contact with electrolytic baths 24a, 24b.

In other words, these electrodes 25a, 25b may not be arranged inside electrolytic baths 24a, 24b, but may be electrically connected to the electrolyte that fills these electrolytic baths 24a, 24b.

Further, although chip holding plate 23 made of a resin is used as one for holding sensor chip 14 in the present embodiment, a tube of another resin, a glass plate, a glass tube, or the like may be used.

Next, an operation of the cellular electrophysiological sensor in the present embodiment is described.

First, the insides of above and below electrolytic baths 24a, 24b shown in FIG. 13 are respectively filled with an extracellular fluid and an intracellular fluid, while a bubble is kept out, and the extracellular fluid and the intracellular fluid are respectively brought into contact with electrodes 25a, 25b.

Here, for example in a case of muscle cells of mammals, the extracellular fluid is typically an electrolyte added with $K^+$ ions of 155 mM, $Na^+$ ions of the order of 12 mM, and $Cl^-$ ions of the order of 4.2 mM, and, the intracellular fluid is an electrolyte added with $K^+$ ions of the order of 4 mM, $Na^+$ ions of the order of 145 mM, and $Cl^-$ ions of the order of 123 mM. It should be noted that the electrolyte may be a solution other than the foregoing solution, and may be a solution containing ions of $Ca^{2+}$, $K^+$, $Na^+$, $Cl^-$, and the like which are necessary for the cell to perform an ion-channel activity and being blended appropriately with these elements depending upon the kind of cells and ion channels.

In this state, it is possible to measure a conduction resistance value of the order of 100 kΩ to 10 MΩ between electrodes 25a, 25b. This is because the extracellular fluid or the intracellular fluid is infiltrated into conduction hole 21, to allow conduction between two electrodes 25a, 25b through the extracellular fluid and the intracellular fluid.

Next, when cell 26 is charged from a top side of upper electrolytic bath 24a and lower electrolytic bath 24b is depressurized, cell 26 is pulled to conduction hole 21, to block conduction hole 21. When a cell film of cell 26 closely adheres to a periphery of conduction hole 21, electrical resistance between upper and lower electrolytic baths 24a, 24b comes into a sufficiently high state of being not smaller than 1 GΩ (hereinafter referred to as a "giga-seal state").

When this giga-seal state can be realized, an electrical path not through cell 26 (leak path) can be reduced as much as possible. Hence in the case of changes in potentials inside and outside cell 26 having been generated due to the ion-channel activity of cell 26, even a slight potential difference or current can be detected.

Next, a method for manufacturing sensor chip 14 in the present embodiment is described.

Figure 15:
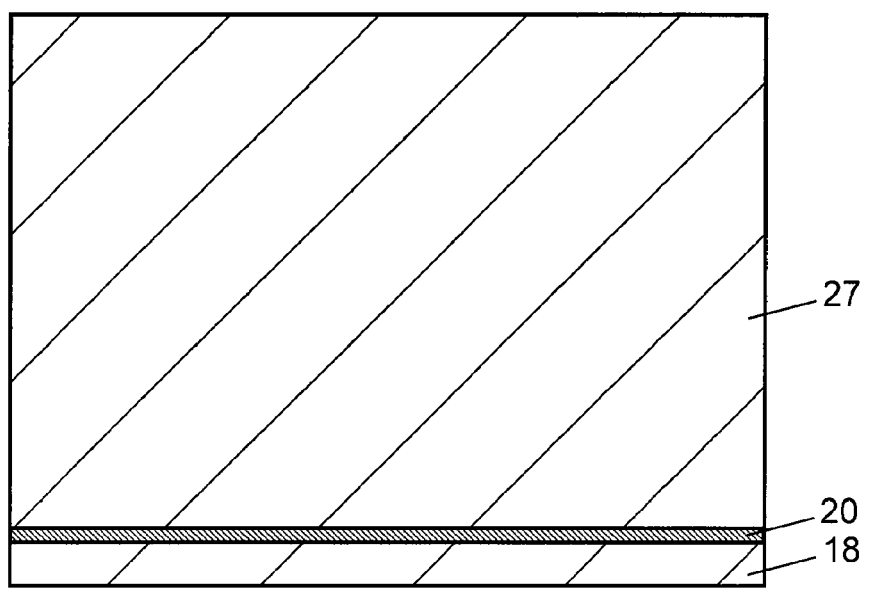
FIG. 15 is a sectional view showing a manufacturing step for the sensor chip in the second embodiment of the present invention.

First prepared is a so-called SOI substrate obtained by sandwiching silicon dioxide layer 20 between silicon layer 18 and silicon layer 27, as shown in FIG. 15. As the SOI substrate used is one where silicon dioxide layer 20 with a large film thickness of 2.0 μm and silicon layer 18 with a film thickness of 5 μm have previously been formed by lamination or CVD.

Silicon layer 18 and silicon dioxide layer 20 are separately dry-etched to form conduction hole 21, and a portion of silicon layer 27 which corresponds to the cavity (portion to become cavity 17 of FIG. 14) is further dry-etched, to form the frame body (portion to become frame body 16 of FIG. 14).

Figure 16:
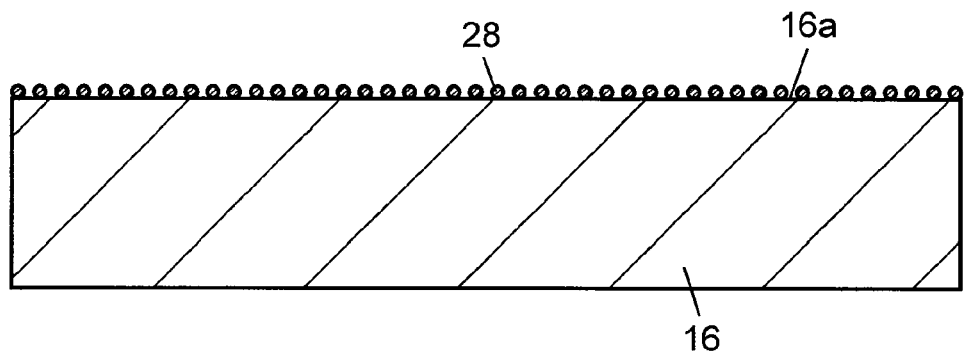
FIG. 16 is an enlarged sectional view of a main part, showing a manufacturing step for the sensor chip in the second embodiment of the present invention.

Subsequently, at least any gas among $CF_4$, $CHF_3$, $C_2F_6$, $C_3F_8$ and $C_4F_8$ is decomposed in plasma, and introduced toward inner wall 16a of frame body 16 made up of silicon layer 27. Then, as shown in FIG. 16, seed layer 28 is formed on inner wall 16a of frame body 16.

This seed layer 28 is a layer made of an organic polymer containing C, H and F elements, and can be formed by decomposing the foregoing fluorocarbon-based gas, such as $CF_4$, $CHF_3$, $C_2F_6$, $C_3F_8$ or $C_4F_8$, in plasma by means of plasma CVD.

It is to be noted that, when these gases are to be decomposed in plasma, the use of ICP (Inductive Coupled Plasma) increases a degree of decomposition of the gases, thereby to facilitate uniform formation of seed layer 28.

It should be noted that in order to uniformly form fibrous projections formed by means of seed layer 28 in a later step, a surface of silicon layer 27 where inner wall 16a of frame body 16 is exposed is desirably made up of only silicon atoms, but the surface may be in the state of being formed with an extremely thin, naturally oxidized film.

Thereafter, when sensor chip 14 is fired in the oxygen atmosphere in the range of 1000° C. to 1100° C., as shown in FIG. 14, fibrous projections 22 made of silicon dioxide are formed on inner wall 16a (corresponding to an area where seed layer 28 is formed in FIG. 16) of frame body 16. According to this method, these fibrous projections 22 come into the state of being bonded with inner wall 16a by direct joining, thereby to have excellent thermal resistance, as shown in the first embodiment.

Moreover, in this firing step, on a side surface of silicon layer 18 or a surface of silicon layer 27 where seed layer 28 is not formed, the fibrous projections are not formed but a thermally oxidized film (not shown) made of silicon dioxide is formed. Since this thermally oxidized film has electrical insulation, in the present embodiment, a leak current through sensor chip 14 can be reduced, thereby contributing to improvement in measurement accuracy of the cellular electrophysiological sensor.

In addition, in the firing step, it is considered that seed layer 28 containing C, H and F elements is destroyed by firing, with no adherence left on inner wall 16a, and an adherence that becomes a factor to inhibit the hydrophilicity is not present.

In the present embodiment, the measurement accuracy of the cellular electrophysiological sensor can be improved. The reason for this is that bubbles that are generated inside cavity 17 of frame body 16 can be reduced.

Figure 37:
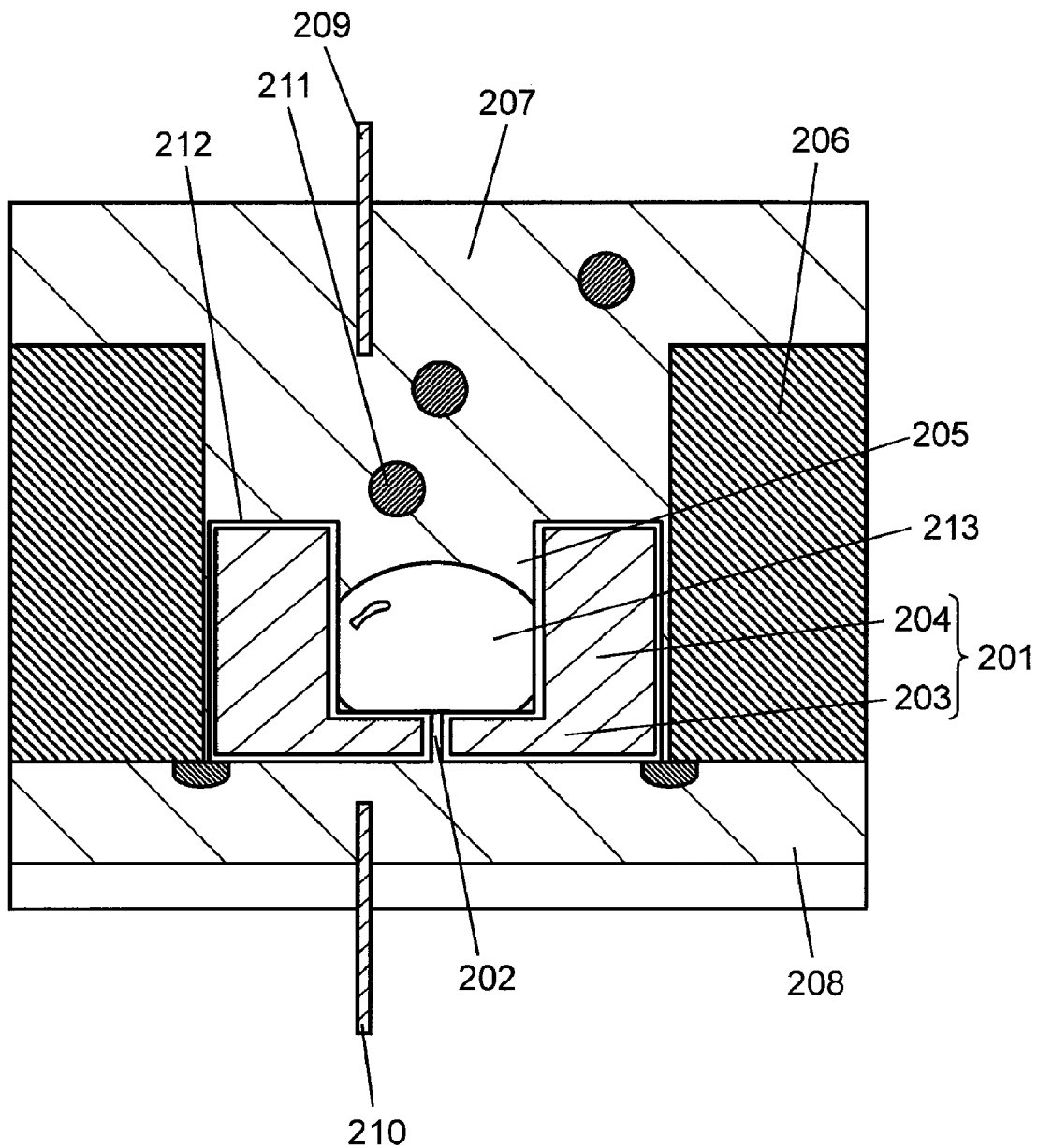
FIG. 37 is a sectional view of a conventional cellular electrophysiological sensor.

Specifically, as shown in FIG. 37, on the surface of conventional sensor chip 201, thermally oxidized film 212 made of silicon dioxide is formed. In this area where this thermally oxidized film 212 is formed, a liquid material significantly affected by surface tension of silicon dioxide, such as water, is strongly pulled by the area surface, and the surface thus has the hydrophilicity.

However, the surface of this thermally oxidized film 212 loses the hydrophilicity when contamination from the outside such as the air adheres to the surface. In other words, this is a state where the surface tension with which the surface pulls water has become smaller. Further, when thermally oxidized film 212 has a small surface area in addition to this state, it results in a relatively considerable loss of the hydrophilicity.

When the hydrophilicity of the inner wall of frame body 204 decreases, for example in filling the inside of cavity 205 with an electrolyte, an air pool cannot be discharged, thus making bubble 213 apt to be generated. There have thus been cases where this bubble 213 inhibits electrical conduction as well as infiltration of the electrolyte or a medicine between above and below conduction hole 202, namely between electrolytic baths 207, 208, leading to reduction in measurement accuracy of the cellular electrophysiological sensor. Further, there have been cases where the adhesiveness between cell 211 and the opening of conduction hole 202 is inhibited, leading reduction in measurement accuracy of the sensor.

In the present embodiment, as shown in FIG. 14, inner wall 16a of frame body 16 is provided with fibrous projections 22 made of silicon dioxide. Further, in an area where these plural fibrous projections 22 are formed, silicon dioxide has an extremely large surface area.

Accordingly, even when the surface tension per unit area becomes smaller due to adhesion of contamination, the tension that pulls water is hardly lost since the whole surface area is large, resulting in that the surface can hold high hydrophilicity for a long period of time. As a consequence, a bubble is less apt to be generated inside cavity 17, thereby allowing improvement in measurement accuracy of the cellular electrophysiological sensor.

Further, in the present embodiment, since being directly joined to the surface of frame body 16 made of silicon, fibrous projections 22 can be formed without using an adhesive or the like, so as to enhance the thermal resistance. Moreover, impurities that come out of the adhesive or the like and cause a measurement error of the sensor are less apt to be mixed into the cellular electrophysiological sensor.

Further, since fibrous projections 22 in the present embodiment are minutely wound or curled, the surface area further increases, thereby contributing to improvement in hydrophilicity.

Increasing the length of fibrous projections 22 and reducing the spacing therebetween can further enhance the hydrophilicity and later-described water retentivity. Moreover, intertwining each of such fibrous projections 22 without superposition on near fibrous projection 22 can further increase the surface area, to enhance the hydrophilicity.

Furthermore, in the present embodiment, since plural fibrous projections 22 are complexly entwined with one another and the spacing therebetween is as extremely narrow as not smaller than 1 µm and not larger than 10 µm, the surface area of silicon dioxide is extremely large, whereby the hydrophilicity is less apt to decrease, consequently making a bubble less apt to be generated.

Furthermore, in the present embodiment, fibrous projections 22 are intended not to be formed on cell capturing face 19. In other words, fibrous projections 22 can be selectively formed in a predetermined position of the silicon layer, and this predetermined position can be arbitrarily set. For this reason, it is possible to prevent formation of fibrous projections 22 on cell capturing face 19 of sensor chip 14 made of silicon dioxide, thereby to maintain the flatness of the surface of cell capturing face 19.

Therefore, as shown in FIG. 13, it is possible to make cell 26 and cell capturing face 19 closely adhere to each other so as to be held. This enhances the adhesiveness of cell 26 and an opening of conduction hole 21, namely the giga-seal state, resulting in improvement in measurement accuracy of the cellular electrophysiological sensor.

It is to be noted that, when silicon dioxide layer 20 has a film thickness of at least 1000 Å, fibrous projections 22 are not formed on its surface, and these fibrous projections 22 can be selectively formed on the silicon layer.

Further, when cell capturing face 19 is configured of silicon dioxide layer 20, since this silicon dioxide layer 20 has high electrical insulation, a leak current through the surface or the inside of sensor chip 14 can be reduced, so as to improve the measurement accuracy of the cellular electrophysiological sensor.

Moreover, although cell capturing face 19 may be configured of a silicon dioxide layer by thermal oxidation, using the silicon dioxide layer in the SOI substrate as in the present embodiment can facilitate to increase the thickness of the silicon dioxide layer. Therefore, in an electrical path through the sensor chip, a stray capacitance component can be made very small, thereby to have a significant effect on reduction in leak current.

Figure 17:
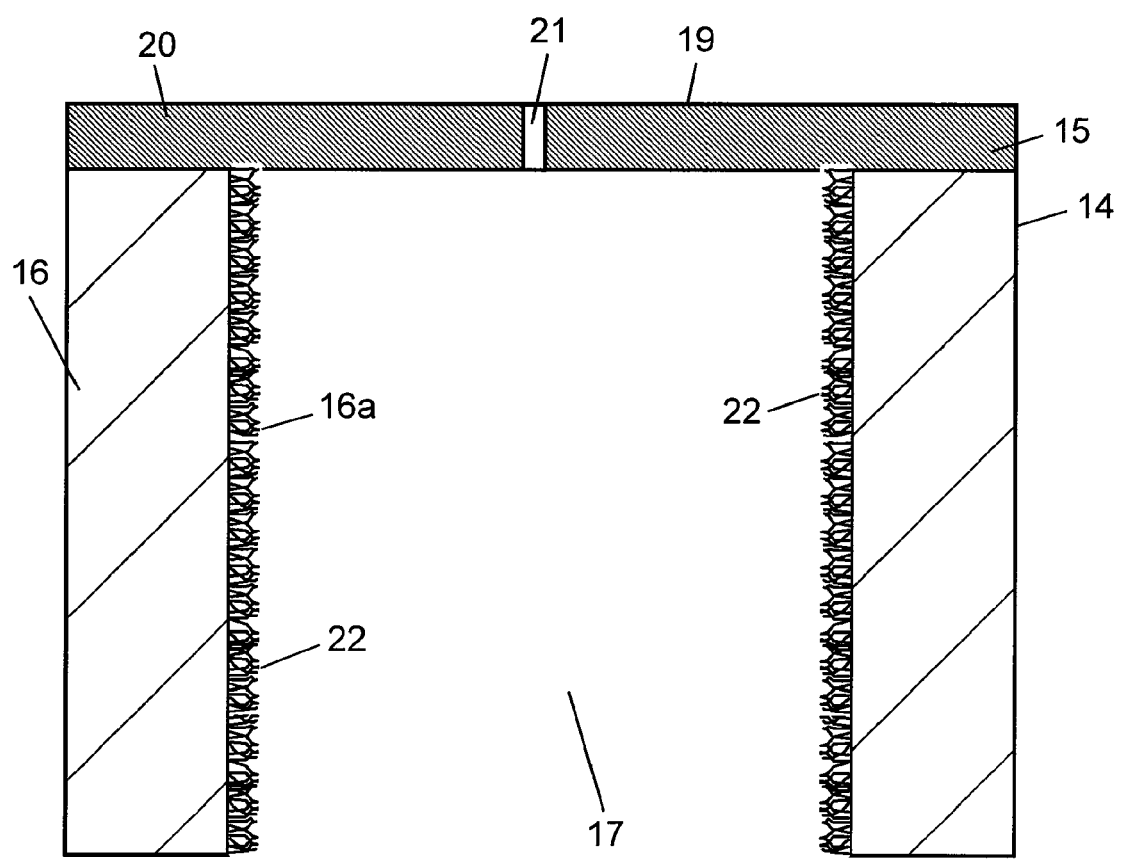
FIG. 17 is a sectional view of the sensor chip in the second embodiment of the present invention.

It is to be noted that, although thin plate 15 is configured of the laminated body of silicon layer 18 and silicon dioxide layer 20 to become cell capturing face 19 in the present embodiment, thin plate 15 may, for example, be formed of only silicon dioxide layer 20 as shown in FIG. 17. Further, as shown in FIG. 17, frame body 16 may be arranged on the under surface of thin plate 15.

In addition, although fibrous projections 22 are formed in almost the whole area of inner wall 16a of frame body 16 in the present embodiment, they may be formed only in a partial area. As methods for partially forming fibrous projections 22, two examples are cited below.

Figure 18:
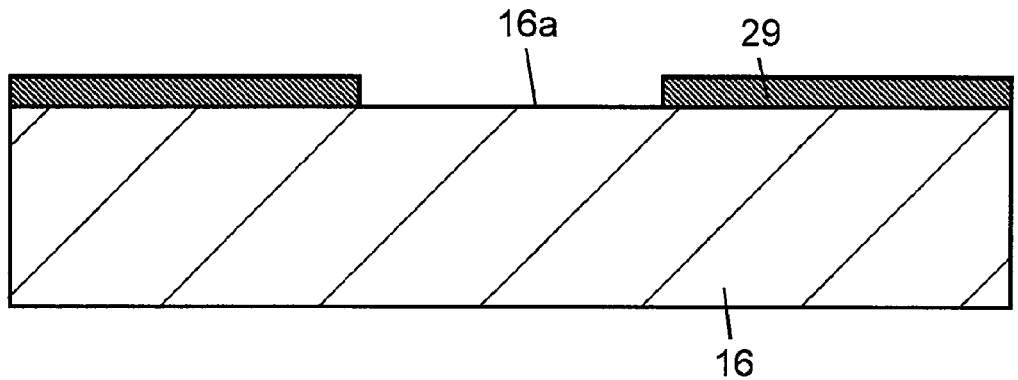
FIG. 18 is an enlarged sectional view of the main part, showing a manufacturing step for the sensor chip in the second embodiment of the present invention.
Figure 19:
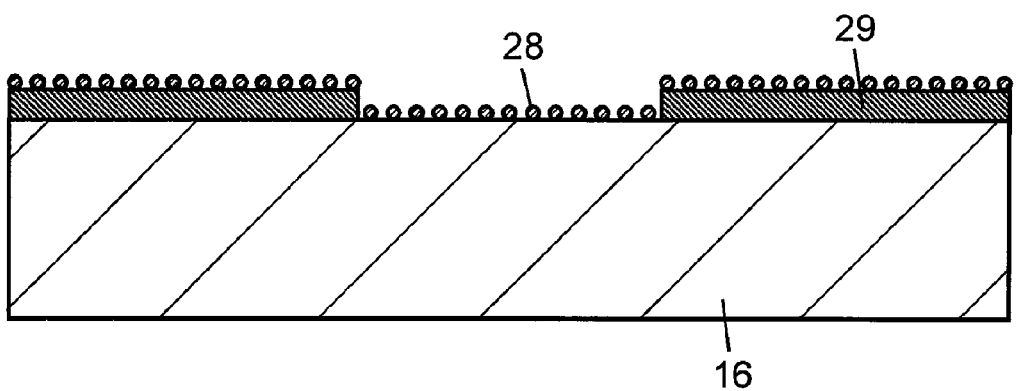
FIG. 19 is an enlarged sectional view of the main part, showing a manufacturing step for the sensor chip in the second embodiment of the present invention.

A first method is that an area where fibrous projections 22 are not to be formed is previously covered with protective layer 29 made of a resin or silicon dioxide, as shown in FIG. 18, and subsequently, seed layer 28 is formed as shown in FIG. 19.

Figure 20:
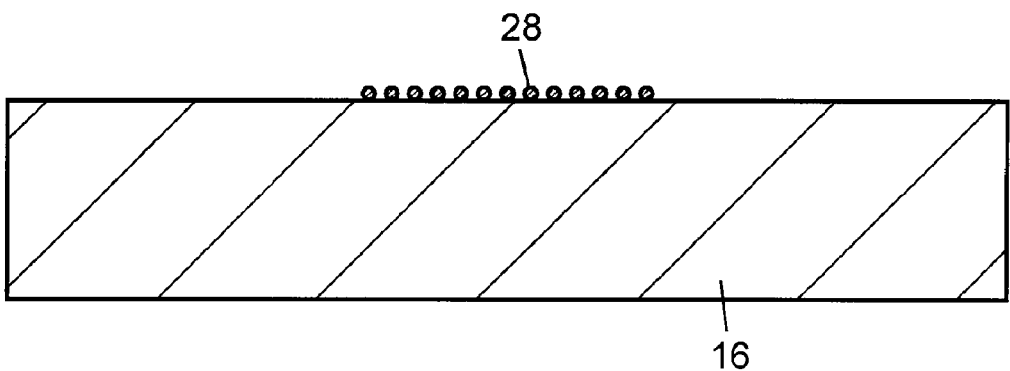
FIG. 20 is an enlarged sectional view of the main part, showing a manufacturing step for the sensor chip in the second embodiment of the present invention.
Figure 21:
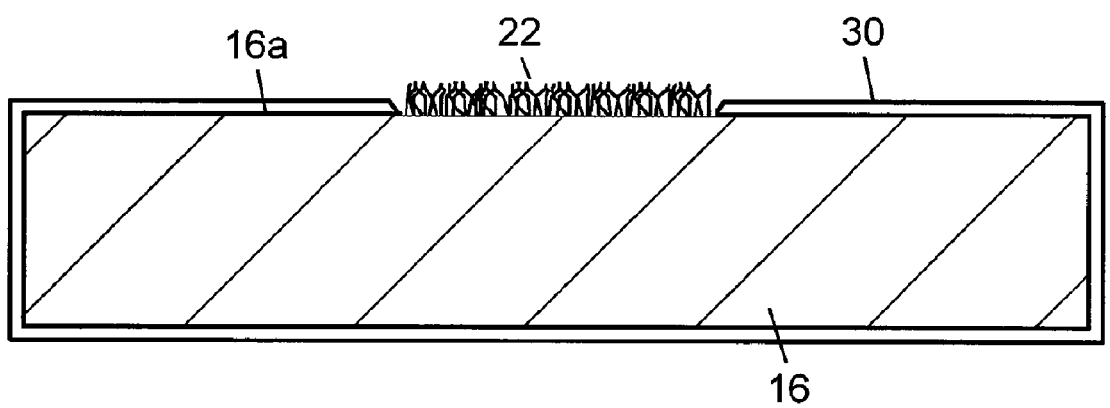
FIG. 21 is an enlarged sectional view of the main part, showing a manufacturing step for the sensor chip in the second embodiment of the present invention.

In this case, when, after formation of seed layer 28, protective layer 29 is removed as shown in FIG. 20 and firing is then performed in the presence of oxygen, it is possible to form fibrous projections 22 in an arbitrary area as shown in FIG. 21. At this time, insulative, thermally oxidized film 30 is formed in the area where seed layer 28 is not formed, so that a leak current through the surface of frame body 16 can be reduced.

It should be noted that in the case of forming seed layer 28 by plasma CVD, this seed layer 28 has relatively strong medicine resistance, thereby facilitating selective removal of only protective layer 29 by chemical treatment using a medicine.

Further, since this seed layer 28 has the medicine resistance, after formation of seed layer 28, it is possible to perform patterning processing on seed layer 28 by means of a normal photolithographic technique. This method is advantageous in that not only patterning on seed layer 28 but also etching processing on frame body 16 can be performed, so as to form a structure having a more complex shape.

Figure 22:
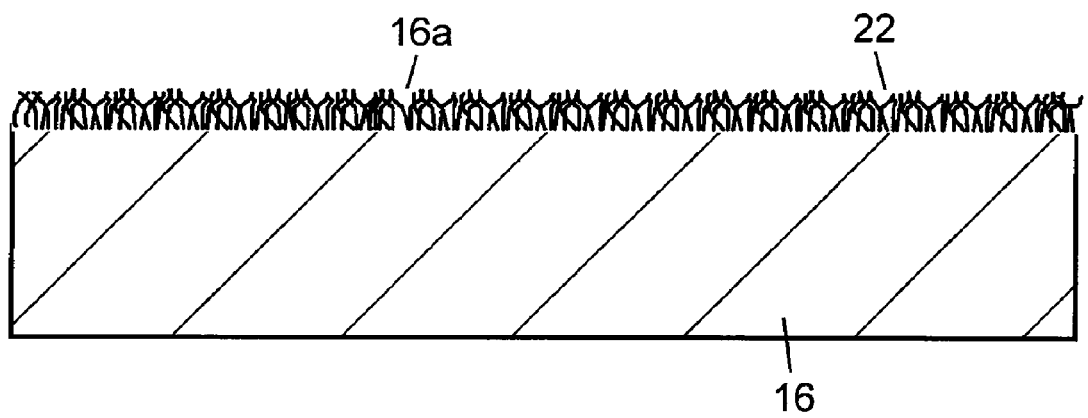
FIG. 22 is an enlarged sectional view of the main part, showing a manufacturing step for the sensor chip in the second embodiment of the present invention.
Figure 23:
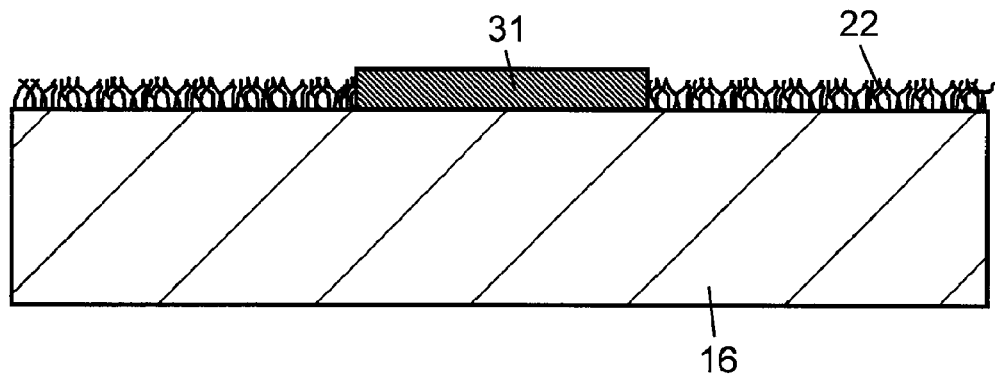
FIG. 23 is an enlarged sectional view of the main part, showing a manufacturing step for the sensor chip in the second embodiment of the present invention.

Moreover, as a second method for partially forming fibrous projections 22, there exists a method in which fibrous projections 22 are formed on inner wall 16a of frame body 16 as shown in FIG. 22, and thereafter, an area where fibrous projections 22 are desired to be left is covered with protective layer 31 made of a resin, as shown in FIG. 23.

Figure 24:
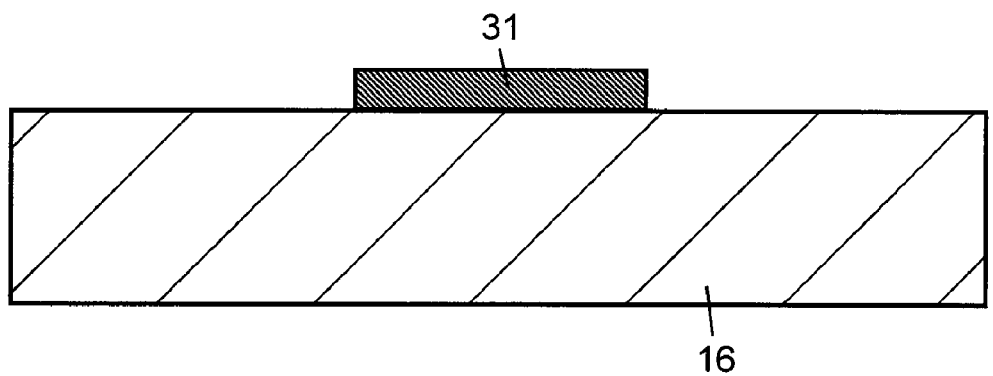
FIG. 24 is an enlarged sectional view of the main part, showing a manufacturing step for the sensor chip in the second embodiment of the present invention.
Figure 25:
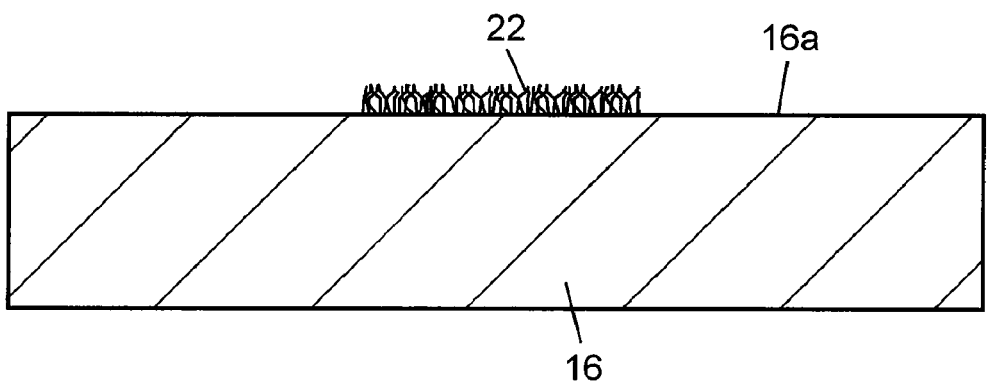
FIG. 25 is an enlarged sectional view of the main part, showing a manufacturing step for the sensor chip in the second embodiment of the present invention.

In this case, fibrous projections 22 in the area where the fibrous projections are desired to be removed may be removed by etching using a normal medicine such as HF or BHF as shown in FIG. 24, and subsequently, protective layer 31 may be removed as shown in FIG. 25. In this case, the foregoing thermally oxidized film is not formed on the exposed face.

It is to be noted that as the method for removing protective layer 31, it is desirable to remove protective layer 31 by chemical treatment using a solvent or the like. This is because fine fibrous projections 22 are less apt to be broken in the chemical treatment as compared with mechanical treatment.

Third Embodiment

Figure 26:
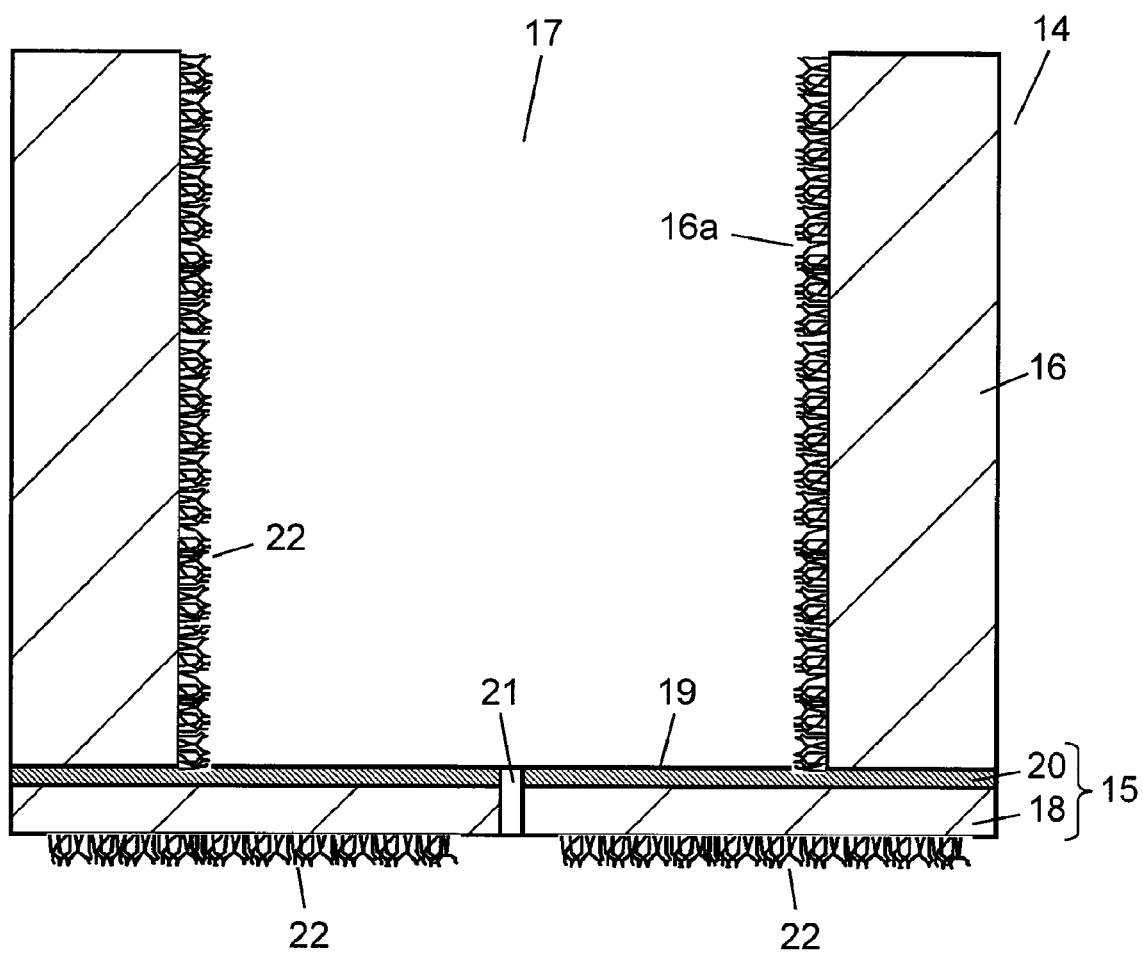
FIG. 26 is a sectional view of a sensor chip in a third embodiment of the present invention.

FIG. 26 is a sectional view of a sensor chip in a third embodiment of the present invention. The present embodiment is different from the second embodiment in that, as shown in FIG. 26, fibrous projections 22 are formed not only on inner wall 16a of frame body 16, but also on an under surface of silicon layer 18 in thin plate 15. Further, in the present embodiment, fibrous projections 22 are formed so as to surround a periphery of conduction hole 21.

This can reduce generation of a bubble also on the under surface of thin plate 15. Specifically, when a bubble is generated on the under surface of the thin plate, that bubble is drifted to be located directly underneath conduction hole 21, thereby to inhibit electrical conduction between the above and below conduction hole 21, or make absorption of a cell more difficult. This may result in reduction in measurement accuracy of the cellular electrophysiological sensor.

As opposed to this, in the present embodiment, since fibrous projections 22 capable of holding the hydrophilicity for a long period of time are formed on the under surface of thin plate 15, bubbles that are generated on the under surface of thin plate 15 can be reduced, thereby leading to improvement in measurement accuracy of the cellular electrophysiological sensor.

Further, in the present embodiment, a phenomenon in which dust is accumulated inside conduction hole 21 in the manufacturing steps can be reduced, thereby improving the measurement accuracy of the cellular electrophysiological sensor.

This is because the area with high water retentivity is provided on the periphery of conduction hole 21 on the under surface of thin plate 15.

Specifically, after being formed by dry-etching or the like, sensor chip 14 is subjected to a cleaning step and a drying step, to be mounted in the cellular electrophysiological sensor.

Here, a cleaning liquid, such as alcohol or water, used in the cleaning step is left inside minute conduction hole 21 and difficult to dry. Therefore, there have been cases where dust having adhered to the surface of sensor chip 14 (e.g. residue of a resist mask or a natural oxidized film) is gradually pulled to the water left inside conduction hole 21 as drying progresses, and drying is performed while the dust is in the state of being accumulated inside conduction hole 21. There has conventionally been a problem in that this dust makes it difficult to attempt for electrical conduction between the above and below conduction hole 21, or inhibits absorption of a cell, leading to reduction in measurement accuracy of the cellular electrophysiological sensor.

As opposed to this, in the present embodiment, hydrophilic fibrous projections 22 are formed as entwined with each other so as to surround conduction hole 21 at a predetermined spacing therefrom. Hence the area where fibrous projections 22 are formed has very high water retentivity.

Accordingly, in the present embodiment, in the step for drying sensor chip 14, a liquid is held in the area where fibrous projections 22 are formed for a long period of time, and dust is pulled to this area where fibrous projections 22 are formed as drying of the surface of silicon layer 18 progresses. This can result in reduction in dust accumulated in conduction hole 21, so as to improve the measurement accuracy of the cellular electrophysiological sensor.

It is to be noted that, although there are respective cases of arranging cavity 17 of frame body 16 in a lower position and in an upper position in the step for drying sensor chip 14, the phenomenon in which dust is pulled to water as described above often occurs on the upward face at the time of drying. Therefore, the present embodiment is effective particularly in effectively preventing accumulation of dust in conduction hole 21 in the case of performing drying with drying cavity 17 arranged in the lower position.

It is to be noted that descriptions of the other configurations and effects that are similar to those of the second embodiment are omitted.

Fourth Embodiment

Figure 27:
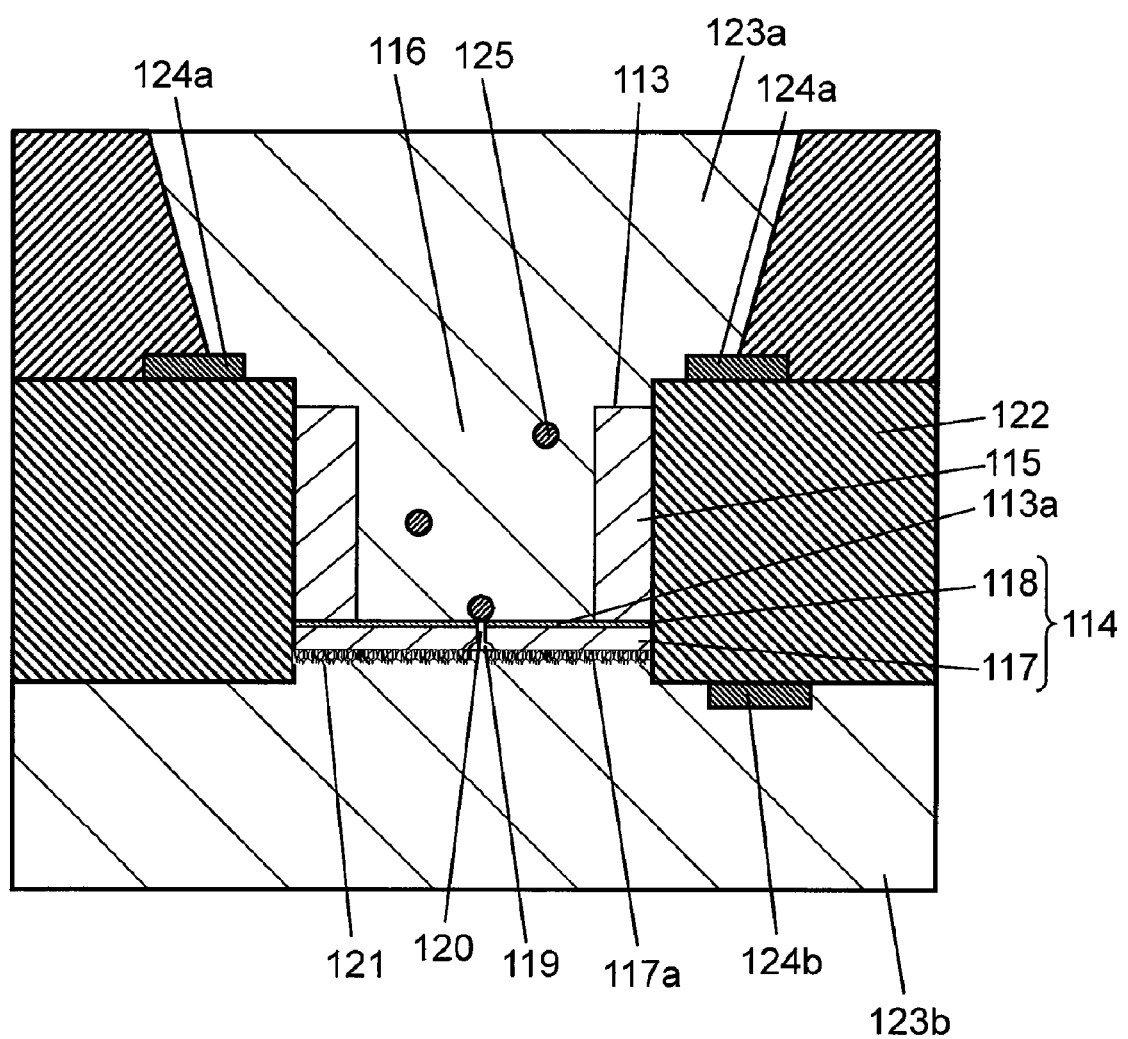
FIG. 27 is a sectional view of a cellular electrophysiological sensor in a fourth embodiment of the present invention.

FIG. 27 is a sectional view of a cellular electrophysiological sensor in a fourth embodiment of the present invention. Sensor chip 113 for the cellular electrophysiological sensor shown in FIG. 27 is provided with thin plate 114 and cylindrical frame body 115 formed and arranged on this thin plate 114. The top of frame body 115 is open and its inside is cavity 116.

This sensor chip 113 is formed of a so-called SOI substrate obtained by sandwiching a silicon dioxide layer between two silicon layers, and thin plate 114 is made up of a laminated body of silicon layer 117 constituting a bottom surface and silicon dioxide layer 118 formed on this silicon layer 117. Plural fibrous projections 121 made of silicon dioxide are directly joined to under surface 117a of silicon layer 117. It is to be noted that silicon dioxide layer 118 serves as cell capturing face 113a on silicon layer 117, and further, frame body 115 is made up of a silicon layer formed on foregoing silicon dioxide layer 118.

Figure 28:
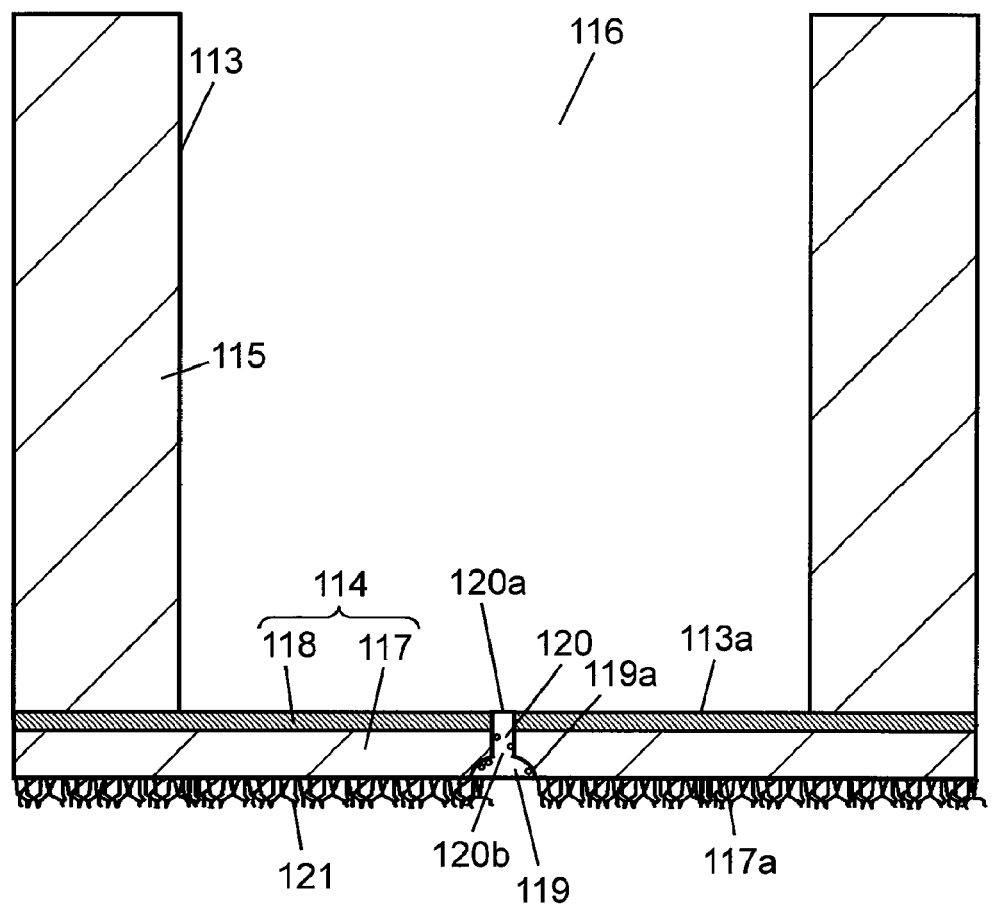
FIG. 28 is a sectional view of a sensor chip in the fourth embodiment of the present invention.

Further, as shown in FIG. 28, in thin plate 114, concave section 119 which is formed on the bottom surface side (under surface 117a side of silicon layer 117) and conduction hole 120 which penetrates from a deepest section of this concave section 119 to a top surface of silicon dioxide layer 118 are formed.

In the present embodiment, plural fibrous projections 121 made of silicon dioxide are directly joined to almost the whole area of under surface 117a of silicon layer 117 in thin plate 114. It is to be noted that these fibrous projections 121 may be formed only in a partial area as described later.

Further, in the present embodiment, a film thickness of silicon layer 117 in thin plate 114 is formed to have a film thickness of about 15 μm, for example, silicon dioxide layer 118 is formed to have a thickness of about 2.0 μm, and silicon layer 117 is formed to have a thickness of about 400 μm.

Concave section 119 has a semispherical shape with a diameter of about 20 μm, and conduction hole 120 has a diameter of about 3 μm and a depth of about 7.0 μm. Here, when conduction hole 120 is to capture a cell with a diameter of 10 to 20 μm, it desirably has a diameter of not smaller than 1 μm and not larger than 5 μm, and a depth of not smaller than 1 μm and not larger than 10 μm. Therefore, when silicon layer 117 is excessively thick, concave section 119 may be provided for adjustment as in the present embodiment.

Further, in the present embodiment, the overall length of fibrous projections 121 is from not smaller than 1.0 μm and not larger than 200 μm, the thickness thereof is not smaller than 0.01 μm and not larger than 10.0 μm, and the spacing between plural fibrous projections 121 is not smaller than 1.0 μm and not larger than 10 μm.

Moreover, these fibrous projections 121 are ones having been grown until being minutely wound or curled in order to have a larger surface area, and fibrous projections 121 each have a wavy shape and are densely formed in a mutually entwined state.

Furthermore, in the present embodiment, foregoing sensor chip 113 is used for the cellular electrophysiological sensor shown in FIG. 27.

The cellular electrophysiological sensor shown in FIG. 27 is provided with: sensor chip 113; chip holding plate (holding section) 122, into which this sensor chip 113 is inserted and which holds a side surface of sensor chip 113; electrolytic baths 123a, 123b arranged above and below sensor chip 113; and electrodes 124a, 124b arranged respectively in electrolytic baths 123a, 123b. In addition, even when these electrodes 124a, 124b are not arranged inside electrolytic baths 123a, 123b, they may be electrically connected to the electrolyte that fills these electrolytic baths 123a, 123b.

It should be noted that, although chip holding plate 122 made of a resin is used as one for holding sensor chip 113 in the present embodiment, a resin tube formed of another resin, a glass plate, a glass tube, or the like may be used.

Next, an operation of the cellular electrophysiological sensor in the present embodiment is described.

First, the insides of above and below electrolytic baths 123a, 123b shown in FIG. 27 are respectively filled with an extracellular fluid and an intracellular fluid, while a bubble is kept out, and the extracellular fluid and the intracellular fluid are respectively brought into contact with electrodes 124a, 124b.

Here, for example in a case of muscle cells of mammals, the extracellular fluid is typically an electrolyte added with $K^+$ ions of 155 mM, $Na^+$ ions of the order of 12 mM, and $Cl^-$ ions of the order of 4.2 mM. Further, the intracellular fluid is an electrolyte added with $K^+$ ions of the order of 4 mM, $Na^+$ ions of the order of 145 mM, and $Cl^-$ ions of the order of 123 mM.

In this state, it is possible to measure a conduction resistance value in the range of the order of 100 k$\Omega$ to 10 M$\Omega$ between electrodes 124a, 124b. This is because the extracellular fluid or the intracellular fluid is infiltrated into conduction hole 120, to allow conduction between two electrodes 124a, 124b through the extracellular fluid and the intracellular fluid.

Next, when cell 125 is charged from a top side of upper electrolytic bath 123a and lower electrolytic bath 123b is depressurized, cell 125 is pulled to an opening (corresponding to opening 120a of FIG. 28) of conduction hole 120, to block opening 120a of conduction hole 120, and a cell film closely adheres to a periphery of conduction hole 120. Thereby, electrical resistance between this opening 120a and a lead-out port (corresponding to lead-out port 120b of FIG. 28), namely between upper and lower electrolytic baths 123a, 123b, comes into a sufficiently high state of being not smaller than 1 G$\Omega$ (hereinafter referred to as a "giga-seal state").

When this giga-seal state can be realized, an electrical path not through cell 125 becomes almost nonexistent. Hence in the case of changes in potentials inside and outside cell 125 having been generated due to the ion-channel activity of cell 125, even a slight potential difference or current can be measured with high accuracy.

Next, a method for manufacturing the sensor chip in the present embodiment is described.

Figure 29:
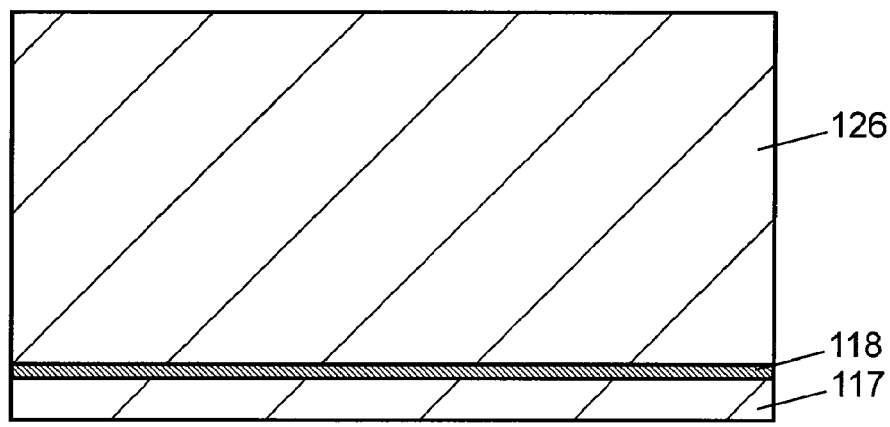
FIG. 29 is a sectional view showing a manufacturing step for the sensor chip in the fourth embodiment of the present invention.

First prepared is a so-called SOI substrate obtained by sandwiching silicon dioxide layer 118 between silicon layer 117 and silicon layer 126, as shown in FIG. 29. As the SOI substrate used is one where, for example, silicon dioxide layer 118 with a large film thickness of the order of 2.0 μm has previously been formed by lamination or the like.

Figure 30:
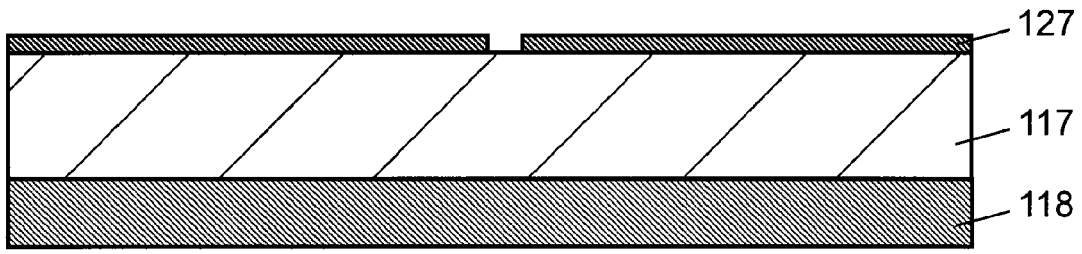
FIG. 30 is a sectional view showing a manufacturing step for the sensor chip in the fourth embodiment of the present invention.

Therefore, as shown in FIG. 30, mask 127 is placed on silicon layer 117. It should be noted FIG. 30 represents only a thin-plate portion (corresponding to thin plate 114 of FIG. 28) made up of silicon layer 117 and silicon dioxide layer 118, omitting a silicon layer (corresponding to silicon layer 126 of FIG. 29) to become a frame body (corresponding to frame body 115 of FIG. 28).

Figure 31:
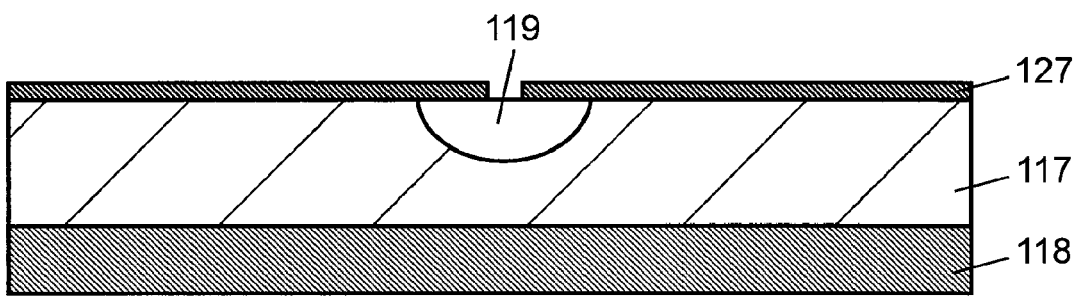
FIG. 31 is a sectional view showing a manufacturing step for the sensor chip in the fourth embodiment of the present invention.

Next, as shown in FIG. 31, an etching gas is sprayed from the above of mask 127 by dry etching technique, to form concave section 119 at the center of silicon layer 117.

As the gas used at this time, a gas for selectively etching silicon is used, and examples thereof may include $SF_6$, $XeF_2$ and a mixed gas of these gases. Since these gases act to promote etching of silicon in a horizontal direction as well as a depth direction, silicon layer 117 can be etched into semispherical saucer shape.

Further, as the above etching gas, a gas in mixture of carrier gases such as $N_2$, Ar, He and $H_2$ is used. Moreover, a molar ratio of the etching gas to the carrier gas is desirably not larger than 2.0.

Figure 32:
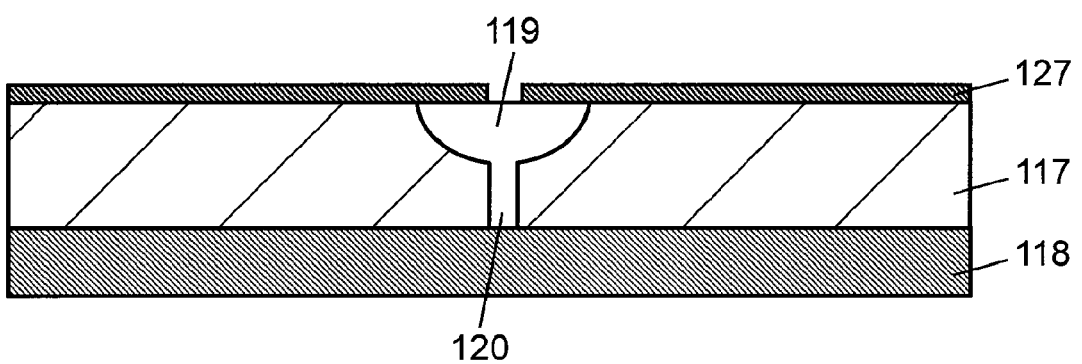
FIG. 32 is a sectional view showing a manufacturing step for the sensor chip in the fourth embodiment of the present invention.

Next, as shown in FIG. 32, by the dry etching technique using ICP plasma, a gas (hereinafter referred to as "promotion gas") for promoting etching of silicon and a gas (hereinafter referred to as "suppression gas") for suppressing the etching are alternately introduced from the above of mask 127, to form conduction hole 120 in silicon layer 117.

As the suppression gas, for example, $C_4F_8$ or $CHF_3$ is preferably used. In this step, silicon layer 117 is etched during introduction of the promotion gas, and a protective film is formed on an inner wall of an etched portion during introduction of the suppression gas. Therefore, optimizing the combination of these etching gases leads to the progress of etching only immediately under a mask hole of mask 127, thereby allowing the etching processing from the deepest section of concave section 119 to conduction hole 120 in almost vertical shape.

It should be noted that, since etching rates are different between silicon layer 117 and silicon dioxide layer 118, silicon dioxide layer 118 functions as an etching stopping layer, so that conduction hole 120 having a predetermined depth can be formed with high accuracy.

Figure 33:
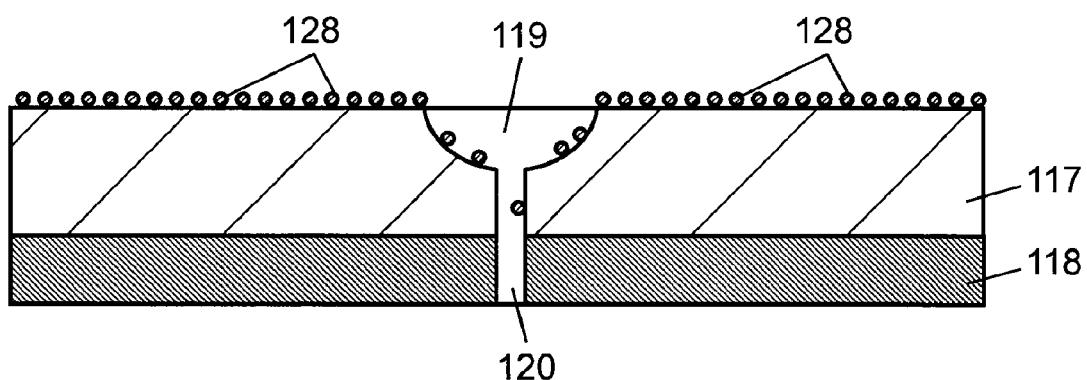
FIG. 33 is a sectional view showing a manufacturing step for the sensor chip in the fourth embodiment of the present invention.

Subsequently, mask 127 is removed, and a surface of silicon layer 117 is exposed, as shown in FIG. 33. In addition, silicon layer 117 exposed at this time is desirably made up of only silicon atoms, but may be in a state where an extremely thin natural oxidized film is formed.

Next, at least any gas among $CF_4$, $CHF_3$, $C_2F_s$, $C_3F_8$ and $C_4F_8$ are decomposed in plasma, and introduced from a surface of silicon layer 117. Then, as shown in FIG. 33, silicon dioxide layer 118 is selectively etched, to form conduction hole 120.

Further, in this step, when the gas is introduced to all over the surface of silicon layer 117, seed layer 128 is formed all over this surface.

This seed layer 128 is a layer made of an organic polymer containing C, H and F elements, and can be formed by decomposing the foregoing fluorocarbon-based gas, such as $CF_4$, $CHF_3$, $C_2F_6$, $C_3F_8$ or $C_4F_8$, in plasma by means of plasma CVD.

As described above, after the thin plate (corresponding to thin plate 114 of FIG. 28) portion has been formed, the silicon layer (corresponding to silicon layer 126 of FIG. 29) to become the frame body (corresponding to frame body 115 of FIG. 28) is dry-etched, to form frame body 115. Since this step is the dry-etching method using ICP plasma as in the step for forming conduction hole 120 in silicon layer 117, a description thereof is omitted.

Subsequently, when sensor chip 113 is fired in the oxygen atmosphere at a temperature in the range of 1000° C. to 1100° C., as shown in FIG. 28, fibrous projections 121 made of silicon dioxide are formed on under surface 117a (corresponding to the area where seed layer 128 is formed in FIG. 33) of silicon layer 117. According to this method, these fibrous projections 121 come into the state of being bonded with silicon layer 117 by direct joining, thereby to have excellent thermal resistance.

Moreover, in this firing step, on a side surface of silicon layer 117 or a surface of silicon layer 126 where seed layer 128 is not formed, fibrous projections 121 are not formed but a thermally oxidized film (not shown) made of silicon dioxide is formed. Since this thermally oxidized film has electrical insulation, in the present embodiment, a leak current through sensor chip 113 can be reduced, thereby contributing to improvement in measurement accuracy of the cellular electrophysiological sensor.

In addition, in the firing step, it is considered that seed layer 128 containing C, H and F elements is destroyed on the surface of silicon layer 27 by firing and thus not being a factor to inhibit the hydrophilicity.

Figure 34:
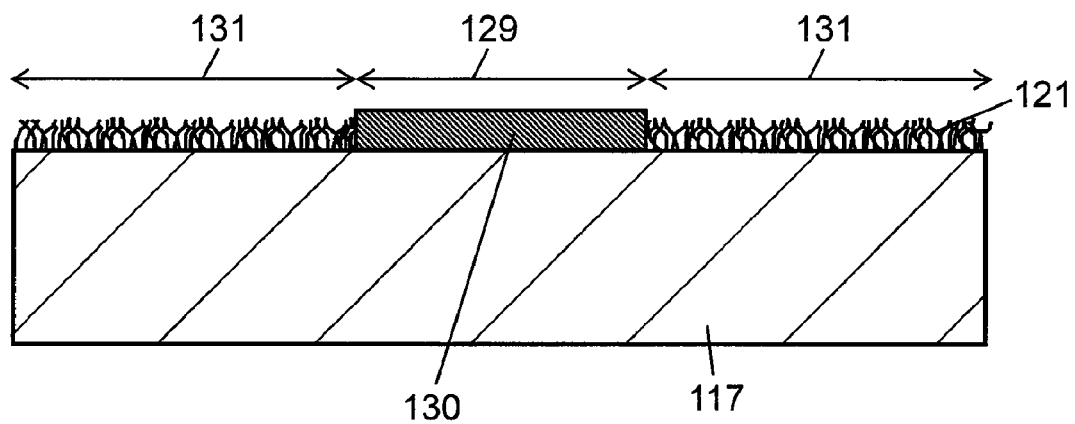
FIG. 34 is a sectional view showing a manufacturing step for the sensor chip in the fourth embodiment of the present invention.

It is to be noted that, although fibrous projections 121 are formed in almost the whole area of under surface 117a of silicon layer 117 in the present embodiment, they may be formed only in a partial area. In this case, for example as shown in FIG. 34, after formation of fibrous projections 121, protective layer 130 made of a resin may be formed in area 129 where fibrous projections 121 are wished to be left. Next, fibrous projections 121 in area 131 where fibrous projections 121 are wished to be removed may be removed by etching, using a normal medicine such as HF or BHF, and protective layer 130 may then be removed. In this case, the foregoing thermally oxidized film is not formed on the exposed face.

It is to be noted that as the method for removing protective layer 130, it is desirable to remove protective layer 130 by chemical treatment. This is because fine fibrous projections 121 are less apt to be broken in the chemical treatment as compared with mechanical treatment.

In the present embodiment, the measurement accuracy of the cellular electrophysiological sensor can be improved.

The reason for this is that bubbles that are generated on under surface 117a of silicon layer 117 in thin plate 114 can be reduced.

Figure 38:
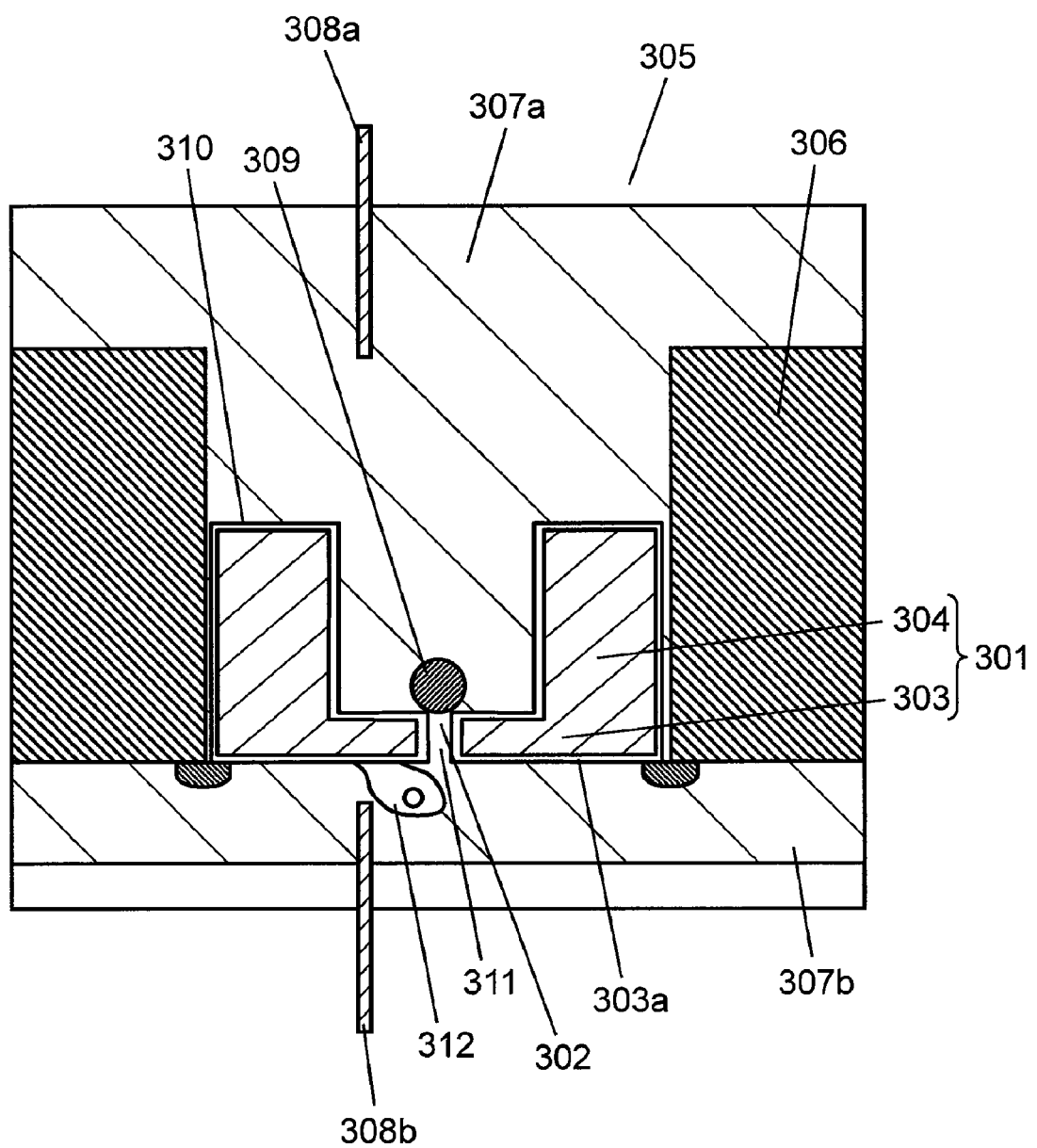
FIG. 38 is a sectional view of another conventional cellular electrophysiological sensor.

Specifically, as shown in FIG. 38, on the surface of conventional sensor chip 301, thermally oxidized film 310 made of silicon dioxide is formed. In this area where thermally oxidized film 310 is formed, a liquid material significantly affected by surface tension of silicon dioxide, such as water, is strongly pulled by the area surface, and the surface thus has the hydrophilicity.

However, the surface of this thermally oxidized film 310 loses the hydrophilicity when contamination from the outside such as the air adheres to the surface. In other words, this is a state where the surface tension with which the surface pulls water has become smaller. Further, when thermally oxidized film 310 has a small surface area in addition to this state, it results in a relatively considerable loss of the hydrophilicity due to adhesion of contamination.

When the hydrophilicity of under surface 303a of thin plate 303 of sensor chip 301 decreases, bubble 312 becomes apt to be generated. Here, when this bubble 312 is generated in the vicinity of lead-out port 311 of conduction hole 302, or drifted to the vicinity of lead-out port 311, electrical conduction between the above and below conduction hole 302, namely between electrolytic baths 307a, 307b, is inhibited. Further, absorption of cell 309 becomes difficult, thereby to inhibit the adhesiveness (giga-sealing properties) between cell 309 and the opening of conduction hole 302.

In the present embodiment, as shown in FIG. 28, under surface 117a of silicon layer 117 is provided with fibrous projections 121 made of silicon dioxide. Further, in an area where these plural fibrous projections 121 are formed, silicon dioxide has an extremely large surface area.

Accordingly, even when the surface tension per unit area becomes smaller due to adhesion of contamination, the whole surface area is large. On this account, the tension that pulls water is hardly lost, resulting in that the surface can hold high hydrophilicity for a long period of time. This can lead to improvement in measurement accuracy of the cellular electrophysiological sensor.

Further, in the present embodiment, since being directly joined to the surface of silicon layer 117, fibrous projections 121 can be formed without using an adhesive or the like, so as to enhance the thermal resistance. Moreover, impurities that cause a measurement error of the sensor (e.g. impurities coming out of the adhesive or the like) are less apt to be mixed into the cellular electrophysiological sensor.

Further, since fibrous projections 121 in the present embodiment are minutely wound or curled, the surface area further increases, thereby contributing to improvement in hydrophilicity.

Increasing the length of fibrous projections 121 and reducing the spacing therebetween can further enhance the hydrophilicity and later-described water retentivity. Moreover, intertwining each of such fibrous projections 121 and near fibrous projection 121 to be densely formed can further increase the surface area, so as to enhance the hydrophilicity.

Moreover, in the present embodiment, plural fibrous projections 121 are complexly entwined, the spacing therebetween is extremely narrow, and the surface area of silicon dioxide is extremely large, whereby the hydrophilicity is less apt to decrease. As a consequence, even when fine bubble seed 119a is generated in concave section 119 shown in FIG. 28, it does not become large, and a bubble is thus less apt to be generated on under surface 117a and the like.

Furthermore, in the present embodiment, fibrous projections 121 are intended not to be formed on cell capturing face 113a. Specifically, since fibrous projections 121 are selectively formed on the silicon layer, fibrous projections 121 are not formed on cell capturing face 113a of sensor chip 113 made of silicon dioxide, thereby to maintain the flatness of the surface of cell capturing face 113a.

Therefore, it is possible to make cell 125 and cell capturing face 113a closely adhere to each other so as to be held. This thus enhances the adhesiveness (giga-sealing properties) of cell 125 and opening 120a of conduction hole 120, resulting in improvement in measurement accuracy of the cellular electrophysiological sensor.

It is to be noted that, when silicon dioxide layer 118 has a film thickness of at least 1000 Å, fibrous projections 121 are not formed on its surface, and these fibrous projections 121 can be selectively formed on the silicon layer.

Further, when cell capturing face 113a is configured of silicon dioxide layer 118, since this silicon dioxide layer 118 has high electrical insulation, a leak current through the surface or the inside of sensor chip 113 can be reduced, so as to improve the measurement accuracy of the cellular electrophysiological sensor. Moreover, although cell capturing face 113a may be configured of a silicon dioxide layer by thermal oxidation, using the silicon dioxide layer in the SOI substrate as in the present embodiment can increase the thickness of the silicon dioxide layer. Therefore, in an electrical path through sensor chip 113, a stray capacitance component can be made very small, thereby to have a significant effect on reduction in leak current.

Fifth Embodiment

Figure 35:
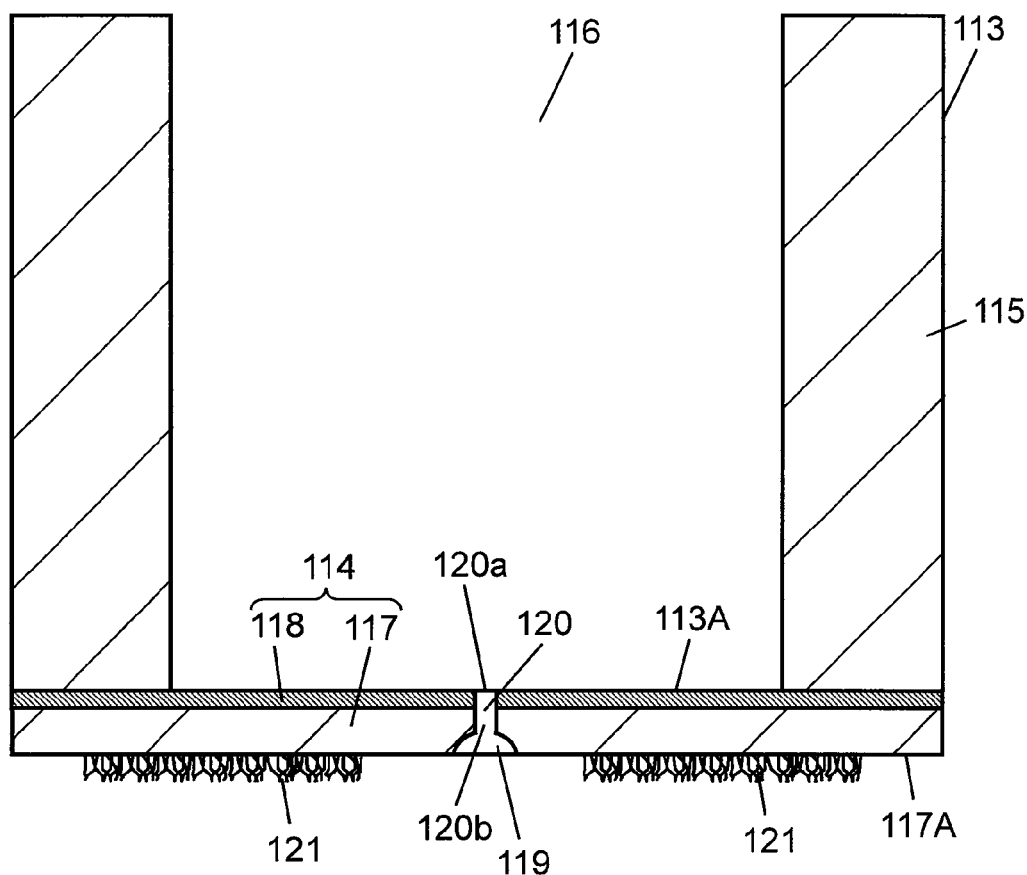
FIG. 35 is a sectional view of a sensor chip in a fifth embodiment of the present invention.

FIG. 35 is a sectional view of a sensor chip in a fifth embodiment of the present invention. The present embodiment is different from the fourth embodiment in that, as shown in FIG. 35, fibrous projections 121 are formed in partial area of under surface 117a of silicon layer 117. In other words, fibrous projections 121 of the present embodiment are not formed on the inner walls of concave section 119 and conduction hole 120. Fibrous projections 121 of the present embodiment are formed so as to surround the periphery of lead-out port 120b of conduction hole 120 and concave section 119 at a predetermined spacing from lead-out port 120b and concave section 119.

Therefore, as in the fourth embodiment, bubbles that are generated below sensor chip 113 can be reduced, and further, dust that is accumulated inside concave section 119 or conduction hole 120 can be reduced, so as to improve the measurement accuracy of the cellular electrophysiological sensor. This dust reduction effect is detailed later.

As a method for partially forming fibrous projections 121 as in the present embodiment, a first method is that, as in the fourth embodiment, after formation of fibrous projections 121, an area where fibrous projections 121 are desired to be left is covered with a protective layer, and fibrous projections 121 are then removed in an area where fibrous projections 121 are unneeded.

Figure 36:
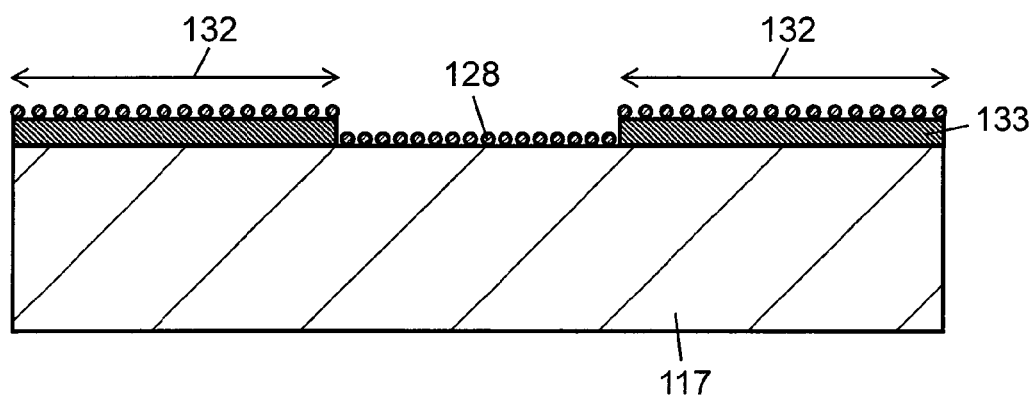
FIG. 36 is a sectional view showing a manufacturing step for the sensor chip in the fifth embodiment of the present invention.

Further, a second method is that, as shown in FIG. 36, area 132 where fibrous projections are not to be formed is previously covered with protective layer 133 made of a resin or silicon dioxide, and seed layer 128 is then formed. In this case, when, after formation of seed layer 128, protective layer 133 is removed and the sensor chip (corresponding to sensor chip 113 of FIG. 3) is fired in the oxygen atmosphere, it is possible to form fibrous projections 121 in an arbitrary predetermined area.

It should be noted that, as in the fourth embodiment, when seed layer 128 is formed by plasma CVD, this seed layer 128 has relatively strong medicine resistance, thereby facilitating selective removal of only protective layer 133 by chemical treatment using a medicine.

Further, since this seed layer 128 has the medicine resistance, after being formed, seed layer 128 can be subjected to patterning processing by means of normal photolithographic technique. This method is advantageous in that it is possible not only to perform patterning on seed layer 128 but also to perform etching processing on frame body 115, so as to form a structure having a more complex shape.

In the present embodiment, on the under surface of sensor chip 113, dust inside concave section 119 and conduction hole 120 can be reduced, so as to improve the measurement accuracy of the cellular electrophysiological sensor.

The reason for this is that the area with high water retentivity is provided on the periphery of concave section 119 and lead-out port 120b of conduction hole 120.

Specifically, after being formed by dry-etching or the like, sensor chip 113 is subjected to a cleaning step and a drying step, to be mounted in the cellular electrophysiological sensor.

Here, a cleaning liquid (e.g. alcohol, water, etc.) used in the cleaning step is left in concave section 119 of sensor chip 113 and inside conduction hole 120, and difficult to dry. Therefore, dust (e.g. residue of a resist mask, natural oxidized film, etc.) having adhered to the surface of sensor chip 113 is gradually pulled to the water left in concave section 119 or inside conduction hole 120 as drying progresses. Consequently, there have been cases where drying is performed while the dust is in the state of being accumulated in concave section 119 or inside conduction hole 120. There has conventionally been a problem in that this dust makes it difficult to attempt for electrical conduction between the above and below conduction hole 120, or inhibits absorption of a cell, leading to reduction in measurement accuracy of the cellular electrophysiological sensor.

As opposed to this, in the present embodiment, hydrophilic fibrous projections 121 are formed as entwined with each other so as to surround concave section 119 and conduction hole 120 at a predetermined spacing therefrom. Hence the area where fibrous projections 121 are formed has very high water retentivity.

Accordingly, in the present embodiment, in the step for drying sensor chip 113, a liquid is held in the area where fibrous projections 121 are formed for a long period of time, and dust is pulled to the area where fibrous projections 121 are formed as drying of the surface of silicon layer 117 progresses. This can result in reduction in dust accumulated in concave section 119 and conduction hole 120, so as to improve the measurement accuracy of the cellular electrophysiological sensor.

It is to be noted that there are respective cases of arranging cavity 116 of frame body 115 in a lower position and in an upper position in the step for drying sensor chip 113. The phenomenon in which dust is pulled to water as described above often occurs on the upward face with cavity 116 of frame body 115 directed upward at the time of drying. Therefore, in the present embodiment, it is possible to effectively prevent dust from being accumulated in conduction hole 120 by forming fibrous projections 121 on silicon layer 117.

It is to be noted that fibrous projections 121 may be not only formed in band form on the whole area surrounding the periphery of lead-out port 120b of conduction hole 120, but may be interspersed along the whole area surrounding the periphery. Further, fibrous projections 121 may be formed as interspersed on the whole area surrounding the periphery.

It is to be noted that descriptions of the other configurations and effects that are similar to those of the fourth embodiment are omitted.

It is to be noted that, although fibrous projections 121 are formed only on thin plate 114 in the present embodiment, they may also be formed on the surface of frame body 115. For example, when fibrous projections 121 are formed also on the inner wall of frame body 115, the hydrophilicity inside frame body 115 is enhanced, to suppress generation of a bubble, thereby further improving the measurement accuracy of the cellular electrophysiological sensor.

Moreover, fibrous projections 121 may also be formed on the side surfaces of thin plate 114 and frame body 115.

INDUSTRIAL APPLICABILITY

The silicon structure and the method for manufacturing the same according to the present invention are useful as being applicable to a biosensor device for measuring a biochemical reaction of a cell or the like, a medicine screening system for performing pharmacological determination at high speed, a fluid control actuator of an inkjet head, and the like.

Further, the sensor chip of the present invention is capable of significantly improving measurement accuracy of a cellular electrophysiological sensor and the like, and hence is useful as being applicable to, for example, the field of medical care where high accurate analyses are required, and to other analyses on pharmacological reactions of cells, and the like.

The invention claimed is:

1. A silicon structure, comprising:
a base; and
a plurality of fibrous projections, which are made of amorphous silicon dioxide, the fibrous projections being directly joined to a silicon-made surface of the base,
wherein the fibrous projections are curved and formed as entwined with one another, and each of the fibrous projections branches out from itself.

2. The silicon structure according to claim 1, wherein the fibrous projections are covalently bonded to the silicon-made surface of the base.

3. The silicon structure according to claim 1, wherein a length of the fibrous projections is not smaller than 1 μm and not larger than 200 μm.

4. The silicon structure according to claim 1, wherein a spacing between the fibrous projections is not smaller than 1 μm and not larger than 10 μm.

5. The silicon structure according to claim 1, wherein a thickness of the fibrous projections is not smaller than 0.01 µM and not larger than 1 µm.

6. The silicon structure according to claim 1, wherein a spacing between the fibrous projections is not smaller than 1 µm and not larger than 10 µm.

7. A method for manufacturing a silicon structure, comprising:
- a first step of forming a seed layer made of an organic polymer in an arbitrary area on a silicon-made surface of a base; and
- a second step of heating the base in an oxygen atmosphere, to form a plurality of fibrous projections made of silicon dioxide in the area where the seed layer is formed.

8. The method for manufacturing a silicon structure according to claim 7, wherein the seed layer is formed by CVD in which at least any gas among $CF_4$, $CHF_3$, $C_2F_6$, $C_3F_8$ and $C_4F_8$ is decomposed in plasma and then laminated.

9. A sensor chip, comprising:
- a thin plate having a conduction hole; and
- a frame body arranged on the thin plate, wherein
- a cell capturing face of the thin plate is formed of a silicon dioxide layer, and the frame body is formed of a silicon layer, and
- a plurality of fibrous projections made of silicon dioxide are directly joined to an inner wall of the frame body.

10. A sensor chip, comprising:
- a thin plate having a conduction hole; and
- a frame body arranged on the thin plate, wherein
- the thin plate is made of a laminated body of a silicon layer and a silicon dioxide layer formed on the silicon layer, and
- a plurality of fibrous projections made of silicon dioxide are directly joined to an under surface of the silicon layer.

11. The sensor chip according to claim 10, wherein the silicon dioxide layer forms a cell capturing face.

12. The sensor chip according to claim 10, wherein the fibrous projections are formed at a predetermined spacing from a lead-out port of the conduction hole, so as to surround a periphery of the lead-out port.

* * * * *